(12) United States Patent
Ishiguro et al.

(10) Patent No.: US 7,112,407 B2
(45) Date of Patent: Sep. 26, 2006

(54) METHOD OF ASSAY OF TARGET NUCLEIC ACID

(75) Inventors: Takahiko Ishiguro, Kanagawa (JP); Juichi Saitoh, Kanagawa (JP); Tetsuya Ishizuka, Kanagawa (JP)

(73) Assignee: Tosoh Corporation, Yamaguchi-ken (JP)

( * ) Notice: Subject to any disclaimer, the term of this patent is extended or adjusted under 35 U.S.C. 154(b) by 301 days.

(21) Appl. No.: 10/687,588

(22) Filed: Oct. 20, 2003

(65) Prior Publication Data

US 2004/0115718 A1    Jun. 17, 2004

Related U.S. Application Data

(63) Continuation of application No. 09/345,761, filed on Jul. 1, 1999, now abandoned.

(30) Foreign Application Priority Data

Jul. 1, 1998    (JP) ................. 10-186434

(51) Int. Cl.
C12Q 1/68     (2006.01)
C07H 21/02    (2006.01)
C07H 21/04    (2006.01)

(52) U.S. Cl. .............. 435/6; 536/23.1; 536/24.3

(58) Field of Classification Search ........... 435/6; 536/23.1, 24.3
See application file for complete search history.

(56) References Cited

U.S. PATENT DOCUMENTS

| 5,130,238 | A | 7/1992 | Malek et al. |
| 5,409,818 | A | 4/1995 | Davey et al. |
| 5,814,447 | A | 9/1998 | Ishiguro et al. |
| 5,824,517 | A | 10/1998 | Cleuziat et al. |
| 6,063,572 | A | 5/2000 | Ishiguro et al. |
| 6,211,354 | B1 | 4/2001 | Horie et al. |

FOREIGN PATENT DOCUMENTS

| EP | 0 855 447 | 7/1998 |
| WO | WO 91 04340 | 4/1991 |
| WO | WO 93 22461 | 11/1993 |

OTHER PUBLICATIONS

Ishiguro et al, *Analytical Biochemistry*, 229:207-213 (1995).
Newton et al, PCR Essential Data, BIOS Scientific Publisher Ltd., pp. 144-149 (1995).
Walker et al, *The Language of Biotechnology*, A Dictionary of Terms, 2nd Ed., pp. 99-100 (1995).
Shibahara et al, *Nucleic Acid Research*, 15(11):4403-4415 (1987).
Ishiguro et al, *Nucleic Acid Research*, 24(24):4992-4997 (1996).

*Primary Examiner*—Ethan Whisenant
(74) *Attorney, Agent, or Firm*—Sughrue Mion, PLLC

(57) ABSTRACT

A simple and accurate method for assay of a single-stranded RNA containing a specific nucleic acids sequence in a sample at almost constant temperature by using at least the following reagents (A) to (I), which comprises a step of adding the reagents (A) to (I) one by one (in any order), in combinations of at least two or all at once and
a step of measuring a fluorescent signal in the presence of the reagent (I) at least once after addition of at least the reagents (A) to (H);
(A) a first single-stranded oligonucleic acid complementary to a sequence neighboring the 5' end of the specific nucleic acids sequence in the single-stranded RNA,
(B) a second single-stranded oligo DNA complementary to a 3'-end sequence within the specific nucleic acids sequence,
(C) an RNA-dependent DNA polymerase,
(D) deoxyribonucleoside triphosphates,
(E) a third single-stranded oligo DNA having (1) a promoter sequence for a DNA-dependent RNA polymerase, (2) an enhancer sequence for the promoter and (3) a 5'-end sequence within the specific nucleic acids sequence, in this order from the 5' end,
(F) a DNA-dependent DNA polymerase,
(G) a DNA-dependent RNA polymerase,

18 Claims, 10 Drawing Sheets

N: No treatment
R: RNaseA treatment
D: DNaseI treatment

○ : Amplification product
■ RNA product (DNase I treatment)
▲ DNA product (RNase A treatment)

SEQUENCE LISTING

<160> NUMBER OF SEQ ID NOS: 7

<210> SEQ ID NO 1
<211> LENGTH: 50
<212> TYPE: DNA
<213> ORGANISM: synthetic construct

<400> SEQUENCE: 1
atttaggtga cactatagaa tacaacactc caccatagat cactcccctg        50

<210> SEQ ID NO 2
<211> LENGTH: 19
<212> TYPE: DNA
<213> ORGANISM: synthetic construct

<400> SEQUENCE: 2
actcgcaagc accctatca        19

<210> SEQ ID NO 3
<211> LENGTH: 11
<212> TYPE: DNA
<213> ORGANISM: synthetic construct

<400> SEQUENCE: 3
gtcgggggga a        11

<210> SEQ ID NO 4
<211> LENGTH: 133
<212> TYPE: RNA
<213> ORGANISM: synthetic construct

<400> SEQUENCE: 4
gggaaagcuu gcaugccugc aggucgacuc uagaggaucc ccggguaccg agcucgaauu        60 ccuuggggc gacacuccac cauagaucac uccccuguga ggaacuacug ucuucacgca        120
gaaagcgucu agc        133

<210> SEQ ID NO 5
<211> LENGTH: 13
<212> TYPE: DNA
<213> ORGANISM: synthetic construct

<400> SEQUENCE: 5
ctcgcggggg ctg        13

<210> SEQ ID NO 6

-continued

```
<211> LENGTH: 315
<212> TYPE: DNA
<213> ORGANISM: Synthetic Construct

<400> SEQUENCE: 6
atttaggtga cactatagaa tacaacactc caccatagat cactccctg tgaggaacta    60 ctgtcttcac gcagaaagcg tctagccatg gcgttagtat gagtgtcgtg cagcctccag   120
gaccccccct cccgggagag ccatagtggt ctgcggaacc ggtgagtaca ccggaattgc   180
caggacgacc gggtcctttc ttggatcaac ccgctcaatg cctggagatt tgggcgtgcc   240
cccgcgagac tgctagccga gtagtgttgg gtcgcgaaag gccttgtggt actgcctgat   300
agggtgcttg cgagt                                                    315

<210> SEQ ID NO 7
<211> LENGTH: 298
<212> TYPE: RNA
<213> ORGANISM: Synthetic Construct

<400> SEQUENCE: 7
gaauacaaca cuccaccaua gaucacuccc cugugaggaa cuacugucuu cacgcagaaa    60
gcgucuagcc auggcguuag uaugaguguc gugcagccuc caggaccccc ccucccggga   120
gagccauagu ggucugcgga accgugagu acaccggaau ugccaggacg accgggcccu   180
uucuuggauc aacccgcuca augccuggag auuugggcgu gccccgcga gacugcuagc   240 cgaguagugu ugggucgcga aaggccuugu gguacugccu gauagggugc uugcgagu    298
```

METHOD OF ASSAY OF TARGET NUCLEIC ACID

This Application is a Continuation of application Ser. No. 09/345,761, filed Jul. 1, 1999; now abandoned, the disclosure of which is incorporated herein by reference.

The present invention relates to a method for assay of a single-stranded RNA containing a specific nucleic acids sequence in a sample, which enables detection and quantification of viral RNA and bacterial mRNA and is effective in diagnosis of infectious diseases and in judging the effects of therapeutic agents for infectious diseases. The present invention also related to a method for producing large amounts of DNA and RNA containing a specific nucleic acids sequence, which is useful for cloning useful genes and exploring unknown genes. The present invention further relates to a reagent set for use in these methods.

Assays of biogenic components require high specificity and sensitivity. Sequence-specific hybridizability of a nucleic acid with a complementary nucleic acid (a nucleic acid probe) is utilized in assays of a specific nucleic acid.

Measurable signaling corresponding to the amount to the hybridization product is essential for quantification of a target nucleic acids sequence. In clinical diagnosis, high-sensitive signaling is required because samples usually contain traces of target nucleic acids.

For quantification of a target nucleic acid in a sample, a method which involves solid phase hybridization of the target nucleic acid with a labeled nucleic acid probe which gives off measurable signals on membranes, beads or gels, called sandwich assay, has been employed. In practice, two nucleic acid probes specific for different sequences within the target nucleic acid are used: a first nucleic acid probe labeled with a dye of a visible color, a fluorescent substance or an enzyme which catalyzes production of such a dye or a fluorescent substance, and a second probe immobilized on a solid phase. These probes are added to a sample and hybridize with the specific nucleic acid in the sample, forming a complex on the solid phase. Then, the reaction mixture is separated into the supernatant and the solid phase to remove the unhybridized first probe (B/F separation). The specific nucleic acid in the sample can be determined by measurement of the label on the solid phase. When the label is an enzyme which catalyzes production of a dye of a visible color or a fluorescent substance, a precursor of the dye or fluorescent substance is added as the substrate of the enzyme to the sample solution after the B/F separation, and the resulting dye or fluorescent substance is measured.

Especially, in diagnosis of virus infections, because clinical samples usually contains the target nucleic acid (viral nucleic acid) in trace amounts, sandwich assay using a chemiluminescent substance as the substrate of the enzyme or preceded by preamplification of the target nucleic acid in samples by polymerase chain reaction (PCR) has been attempted to increase the signal intensity and sensitivity for the purpose of sensitive and reproducible assay.

Another PCR-based method known for assay of a target nucleic acid is competitive PCR. In the method, PCR is performed in the presence of a given concentration of a nucleic acid having a base sequence similar to that of the target nucleic acid (a competitor) in the sample, the concentration of the target nucleic acid is estimated from the amplification level of the target nucleic acid. In practice, a sample is subjected to PCR in the presence of various concentrations of a nucleic acid which has a terminal sequence complementary to a primer and is distinguishable from the amplification product from the target nucleic acid (for example, by the length) by some separation means such as electrophoresis simultaneously.

Homogeneous support-free assay for PCR-based quantification of a target nucleic acid has also been proposed. For example, the present inventors reported an assay method wherein the initial amount of the target nucleic acid is determined by fluorescence measurement of the reaction solution after each PCR cycle during PCR in the presence of a fluorescent intercalative dye (JP-A-5-237000; Igaku-no-Ayumi, 173(12), 959–963 (1995); Analytical Biochemistry, 229, 207–213 (1995)). In the assay method, as the PCR amplification products are double-stranded DNA, a fluorescent intercalative dye which changes its fluorescence characteristic for example, by increasing the fluorescence intensity, upon intercalation into double-stranded nucleic acid, is added to sample solutions prior to PCR amplification, and the fluorescence intensity of the reaction solution is monitored to determine the initial amount of the target nucleic acid from the pattern of the fluorescence enhancement. Further, this method makes it possible to keep track of amplification of the target nucleic acid by fluorometric measurement of the reaction solution in a closed reaction vessel and therefore can obviate the problem of false positive results attributable to carryover of the amplification products because sampling of the reaction solution from the reaction vessel is unnecessary.

At present, the detection or quantification limit of the sandwich assay of a target nucleic acid is at most about $10^5$ copies even if the fist probe labeled with multiple enzyme molecules is used to produce a large amount of a luminescent substance in an enzymatic chemiluminescence system known for a relatively high sensitivity, because the first probe non-specifically adsorbed on the solid support gives off a considerable background signal (background) and therefore produces errors in the measurement of the solid phase hybridization on the surface.

In order to prevent non-specific adsorption of a first probe on a solid support, hydrophilic surface treatment of the support, blocking of the adsorptive sites on the support surface with protein, through washing of the solid support after the B/F separation and use of a high detergency cleaning solution containing a surfactant have been attempted.

However, chemical hydrophilic surface treatment is not applicable to some kinds of supports depending to the material of the support and can be technically difficult. Also, protein coating of the support surface for blocking of the adsorption sites on the support can lead to a different type of non-specific adsorption due to interaction between the protein coat and the nucleic acid segment or the label of the first probe. Washing operations after the B/F separation can not be increased indefinitely due to operational limitations, and the surfactant added to a cleaning solution can induce decomposition of the hybrid formed on the support.

In competitive PCR assay, it is necessary to perform PCR on sample solutions containing a competitor at various concentrations ranging over the predicted target nucleic acid concentration for analysis of one sample. Besides, post-PCR separation of sample solutions withdrawn from the reaction vessels, for example, by electrophoresis is necessary. Therefore, competitive PCR assay is difficult to automate and inappropriate for clinical diagnosis which requires speedy handling of a great number of samples. Further, due to the need to withdraw sample solutions from reaction vessels, the false positive problem attributable to carryover of the amplification products in practical application of the PCR assay remais to be solved.

PCR-based assays in the presence of a fluorescent intercalative dye have a problem that when the sample contains a large amount of other double-stranded DNA such as genomic DNA in addition to the specific nucleic acid, the intercalative dye intercalates into other double-stranded DNA producing a significant background, because it is based on the ability of a fluorescent intercalative dye to intercalate into double-stranded nucleic acid. Further, in PCR-based assays using a pair of oligo DNAs complementary to the specific nucleic acid sequence as the primers for chain elongation, the primers can hybridize each other, depending on their base sequences, and elongate by using each other as templates to produce a primer dimer. Because the intercalation of a fluorescent intercalative dye into double-stranded nucleic acid is not specific, production of such a primer dimer creates a problem of a high background.

The demand for automation in clinical diagnostics likely continues to increase to realize speedy and reproducible analyses of a great number of samples. PCR involves repetitious rapid heating and cooling of reaction solutions and entails strict temperature control during heating and cooling because accuracy and reproducibility of these operations can affect the results of PCR. However, it is not easy to provide a full-automatic instrument having enough incubation ability to satisfy these requirements and a sufficient throughput capacity.

Further, in the case of RNA as viral nucleic acids in most viruses, PCR is preceded by synthesis of cDNA by reverse transcriptase using RNA as the template, and therefore virtually two steps are involved.

For amplification of a target nucleotide at constant temperature, a so-called NASBA method is known. The NASBA method seems easy to automate because heating or cooling is unnecessary, but requires sandwich assay or electrophoretic separation of the amplified RNA and therefore can not solve the problems attributable to these operations.

Accordingly, the object of the present invention is to provide a simple and accurate method for assay of a single-stranded RNA containing a specific nucleic acids sequence in a sample at almost constant temperature without repetitious rapid heating and cooling of reaction solutions in PCR or using a support in measurement of the amplified RNA, wherein all the operations are preferably done in a closed vessel. Another object of the present invention is to provide a simple method for producing a nucleic acid having a specific nucleic acids sequence at almost constant temperature.

The present inventors developed a nucleic acid probe which is complementary to a specific nucleic acids sequence in the target nucleic acid and labeled with a fluorescent intercalative dye so as to give a measurable fluorescent signal on binding to the target nucleic acid (JP-A-7-185599/EP-A-714986/Nucleic Acid Research, 24(24), 4992–4997 (1996)). The nucleic acid probe gives a measurable fluorescent signal on hybridization with the target nucleic acid and therefore enables detection of hybridization and quantification of the hybridization product without separation of the unhybridized probe. Further, the present inventors have established synthesis of an RNA having the specific acid sequence by using a nucleic acid polymerase and nucleic acid primers in the presence of the nucleic acid probe at constant temperature, namely amplification and assay of the target RNA at constant temperature without using a support, preferably in a closed system, and have accomplished the present invention.

According to Claim 1 of the present application, the present invention provides a simple and accurate method for assay of a single-stranded RNA containing a specific nucleic acids sequence in a sample at almost constant temperature by using at least the following reagents (A) to (I), which comprises a step of adding the reagents (A) to (I) one by one (in any order), in combinations of at least two or all at once and a step of measuring a fluorescent signal in the presence of the reagent (I) at least once after addition of at least the reagents (A) to (H);

(A) a first single-stranded oligonucleic acid complementary to a sequence neighboring the 5' end of the specific nucleic acids sequence in the single-stranded RNA,
(B) a second single-stranded oligo DNA complementary to a 3'-end sequence within the specific nucleic acids sequence,
(C) an RNA-dependent DNA polymerase,
(D) deoxyribonucleoside triphosphates,
(E) a third single-stranded oligo DNA having (1) a promoter sequence for a DNA-dependent RNA polymerase, (2) an enhancer sequence for the promoter and (3) a 5'-end sequence within the specific nucleic acids sequence, in this order from the 5' end,
(F) a DNA-dependent DNA polymerase,
(G) a DNA-dependent RNA polymerase,
(H) ribonucleoside triphosphates, and
(I) a fourth single-stranded oligo DNA complementary to the specific nucleic acids sequence which is labeled so that it gives off a measurable fluorescent signal on hybridization with a nucleic acid containing the specific nucleic acids sequence.

According to Claim 21 in the present application, the present invention provides a simple method for producing a nucleic acid having a specific nucleic acids sequence at almost constant temperature by using at least the following reagents (A) to (H), which comprises a step of adding the reagents (A) to (G) one by one (in any order), in combinations of at least two or all at once to a single-stranded DNA having (1) a promoter sequence for a DNA-dependent RNA polymerase, (2) an enhancer sequence for the promoter and (3) the specific nucleic acids sequence, in this order from the 5' end or to a double-stranded DNA consisting of the single-stranded DNA and a complementary DNA strand and a step of measuring a fluorescent signal from the reagent (H) at least once after addition of at least the reagents (A) to (G);

(A) a single-stranded oligo DNA complementary to a 3'-end sequence within the specific nucleic acids sequence,
(B) an RNA-dependent DNA polymerase,
(C) a DNA-dependent DNA polymerase,
(D) deoxyribonucleoside triphosphates,
(E) a DNA-dependent RNA polymerase,
(F) ribonucleoside triphosphates,
(G) a single-stranded DNA having (1) a promoter sequence for a DNA-dependent RNA polymerase, (2) an enhancer sequence for the promoter and (3) a 5'-end sequence within the specific nucleic acids sequence, in this order from the 5' end,
(H) a fourth single-stranded labeled oligo DNA complementary to the specific nucleic acids sequence which gives a measurable fluorescent signal on hybridization with a nucleic acid containing the specific nucleic acids sequence.

According to Claims 24 to 28 in the present application, the present invention also provides a reagent or reagent set for performing the above-mentioned method, and specifically according to Claim 24, the present invention provides a reagent set for performing the method according to Claim 1 or 21., which comprises at least
a first reagent containing the first single-stranded oligonucleic acid,
a second reagent containing tris-acetate, magnesium acetate, potassium acetate, sorbitol and dimethyl sulfoxide,
a third reagent containing dithiothreitol, deoxyribonucleoside triphosphates, ribonucleoside triphosphates, bovine serum albumin, the second single-stranded oligo DNA and the third single-stranded oligo DNA,
a fourth reagent containing an RNA-dependent DNA polymerase, a DNA-dependent DNA polymerase, a DNA-dependent RNA polymerase and an RNase inhibitor and
a fifth reagent containing the fourth single-stranded oligo DNA.

Specifically according to Claim 25, the present invention provides a reagent set for performing the method according to Claim 1 or 21, which comprises at least
a first reagent containing the first single-stranded oligonucleic acid,
a second reagent containing tris-acetate, magnesium acetate, potassium acetate, sorbitol and dimethyl sulfoxide,
a third reagent containing dithiothreitol, deoxyribonucleoside triphosphates, ribonucleoside triphosphates, bovine serum albumin, the second single-stranded oligo DNA, the third single-stranded oligo DNA and the fourth single-stranded oligo DNA and
a fourth reagent containing an RNA-dependent DNA polymerase, a DNA-dependent DNA polymerase, a DNA-dependent RNA polymerase and an RNase inhibitor.

According to Claim 26, the present invention further provides a reagent set for performing the method according to Claim 1 or 21, which comprises at least
a first reagent containing the first single-stranded oligonucleic acid,
a second reagent containing tris-acetate, magnesium acetate, potassium acetate, sorbitol and dimethyl sulfoxide,
a third reagent containing dithiothreitol, deoxyribonucleoside triphosphates, ribonucleoside triphosphates, bovine serum albumin, the second single-stranded oligo DNA and the third single-stranded oligo DNA,
a fourth reagent containing the fourth single-stranded oligo DNA, an RNA-dependent DNA polymerase, a DNA-dependent DNA polymerase, a DNA-dependent RNA polymerase and an RNase inhibitor.

Specifically according to Claim 27, the present invention provides a reagent for performing the method according to Claim 1 or 21, which comprises at least the first single-stranded oligonucleic acid, the second single-stranded oligo DNA, the third single-stranded oligo DNA, the fourth single-stranded oligo DNA, an RNA-dependent DNA polymerase, a DNA-dependent DNA polymerase, a DNA-dependent RNA polymerase, deoxyribonucleoside triphosphates, ribonucleoside triphosphates, tris-acetate, magnesium acetate, potassium acetate, sorbitol, dimethyl sulfoxide, dithiothreitol, bovine serum albumin and an RNase inhibitor, namely a single reagent obtained by mixing them all.

FIG. 1 shows the results of the 2% agarose gel electrophoresis of the product of the PCR using the second and third single-stranded oligo DNAs in Example 1. Lanes 2 to 4: known concentrations of the standard DNA, lanes 5 to 7: 0.2 to 5 µl of the PCR product.
Lane 1. φx174/HaeIII
Lane 2. 363 ng/lane HCV cDNA (1865 bp)
Lane 3. 72.5 ng/lane HCV cDNA (1865 bp)
Lane 4. 14.5 ng/lane HCV cDNA (1865 bp)
Lane 5. PCR product 5 µl/lane
Lane 6. PCR product 1 µl/lane
Lane 7. PCR product 0.2 µl/lane
Lane 8. φx174/HaeIII FIG. 2 shows the results of the 2% agarose gel electrophoresis after the reactions at various magnesium acetate concentrations in Example 2. The arrow indicates the specific product (about 300 bp). The concentrations of magnesium acetate are expressed in terms of final concentration.
N: Negative
Numerals logarithmically denote the initial copy number (/test) of the standard DNA
C1: $10^{10}$ copy/l lane standard DNA
C2: $5 \times 10^{11}$ copy/l lane standard DNA
S: φx174/HaeIII FIG. 3 shows the results of the 2% agarose gel electrophoresis after the reactions at various potassium acetate concentrations in Example 3. The arrow indicates the specific product (about 300 bp). The concentrations of potassium acetate are expressed in terms of final concentration.
N: Negative
Numerals logarithmically denote the initial copy number (/test) of the standard DNA
C1: $10^{10}$ copy/l lane standard DNA
C2: $5 \times 10^{11}$ copy/l lane standard DNA
S: φx174/HaeIII FIG. 4 shows the results of the 2% agarose gel electrophoresis after the reactions at final sorbitol concentrations of 15%, 11.3%, 9% and 7.5% in Example 4. The arrow indicates the specific product (about 300 bp).
N: Negative
Numerals logarithmically denote the initial copy number (/test) of the standard DNA
C1: $10^{10}$ copy/l lane standard DNA
C2: $5 \times 10^{11}$ copy/l lane standard DNA
S: φx174/HaeIII FIG. 5 shows the results of the 2% agarose gel electrophoresis after the reactions in the presence of various concentrations of the standard DNA in Example 5. The arrow indicates the specific product (about 300 bp).

FIG. 6 shows the results of the electrophoresis on a polyacryl amide gel containing 12% urea after the reaction of the 133 mer RNA, the first single-stranded oligo DNA complementary to a neighboring sequence at the 5' end of the specific nucleic acids sequence within the 133 mer RNA and various concentrations of RnaseH in Example 6. The arrows indicate the 133 mer and the 72 mer.
Lane 1. Thermally denatured x174/HaeIII
Lane 2. Tris-acetate buffer $7 \times 10^{-6}$ U/µl RNaseH
Lane 3. Tris-acetate buffer $7 \times 10^{-5}$ U/µl RNaseH
Lane 4. Tris-acetate buffer $7 \times 10^{-4}$ U/µl RNaseH
Lane 5. Tris-acetate buffer $7 \times 10^{-3}$ U/µl RNaseH
Lane 6. Tris-acetate buffer RNaseH without addition of RNaseH
Lane 7. Tris-HCl buffer $10^{-5}$ U/µl RNaseH
Lane 8. Tris-HCl buffer $10^{-4}$ U/µl RNaseH
Lane 9. Tris-HCl buffer $10^{-3}$ U/µl RNaseH
Lane 10. Tris-HCl buffer $10^{-2}$ U/µl RNaseH
Lane 11. Tris-HCl buffer RNaseH without addition of RNaseH FIG. 7 shows the results of the 2% agarose gel electrophoresis after the reactions in the presence of various concentrations of the standard RNA in Example 7. The arrow indicates the specific product (about 300 bp).

Figure 10:
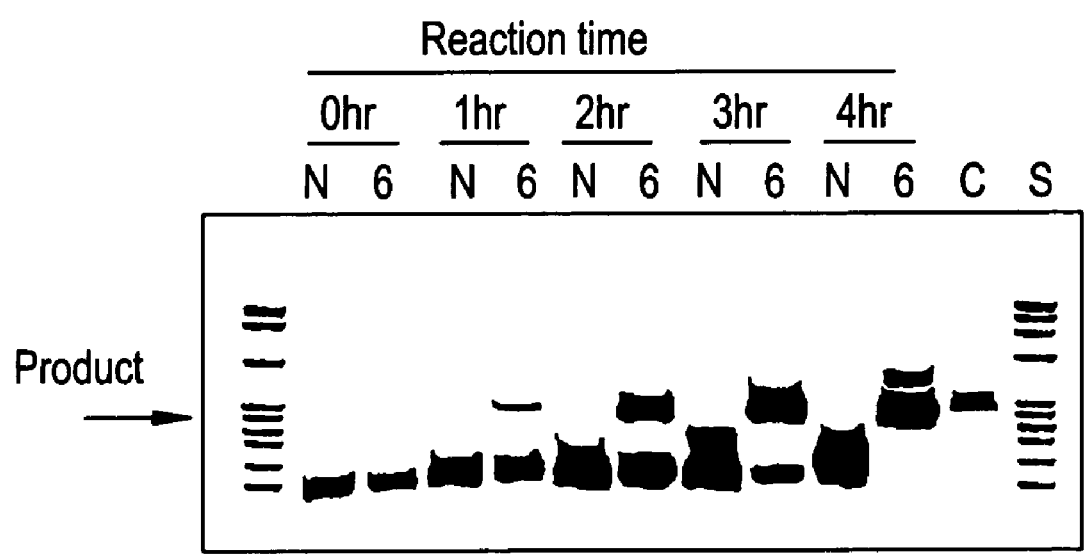
Figure 11:
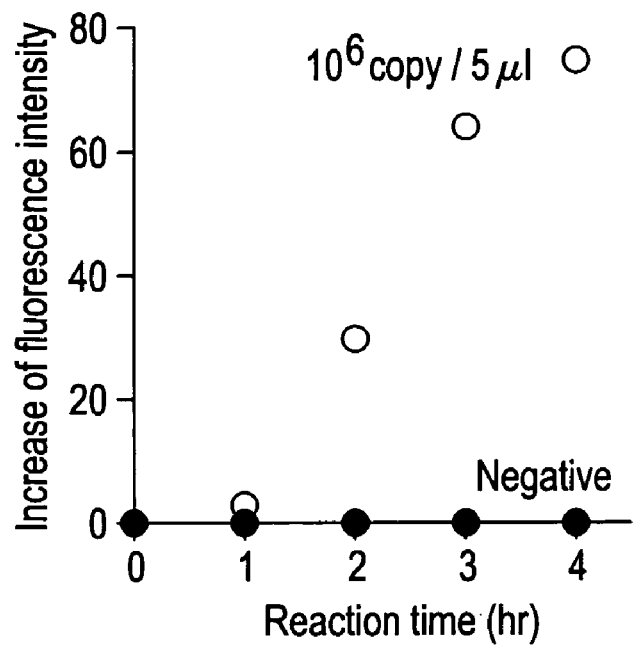

FIG. 10 shows the results of the 2% agarose gel electrophoresis of the products from the standard RNA ($10^6$ copies/5 μl) at various reaction times in Example 10.
N: Negative
6: $10^6$ copy/5 μl, initial copy number of standard DNA
C: $10^{11}$ copy/l lane standard DNA
S: φx174/HaeIII FIG. 11 shows the results of fluorescence measurement after addition of the fourth single-stranded oligo DNA to the products shown in FIG. 10 obtained in Example 10.

Figure 12:
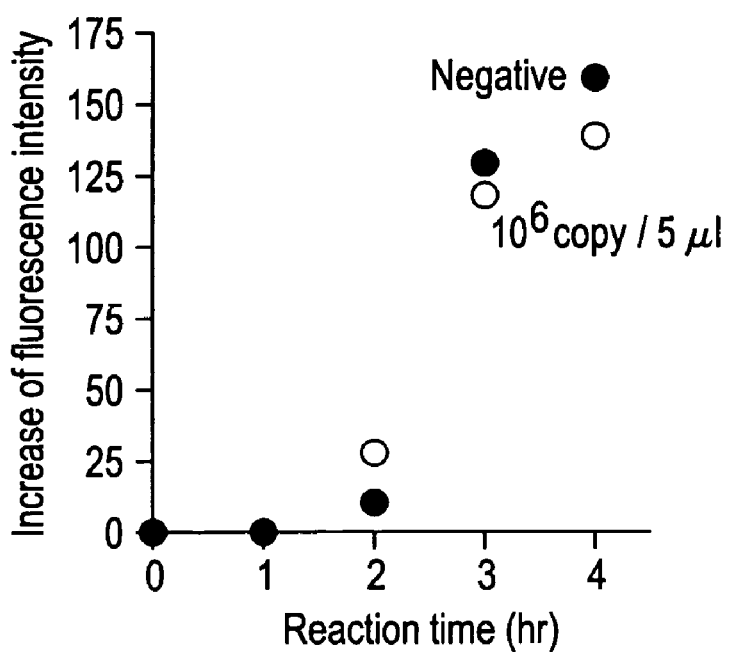

FIG. 12 shows the results of the fluorescence measurement after various times of reactions using the standard RNA ($10^6$ copies/5 μl) in the presence of the fourth single-stranded oligo DNA in Example 11.

Figure 13:
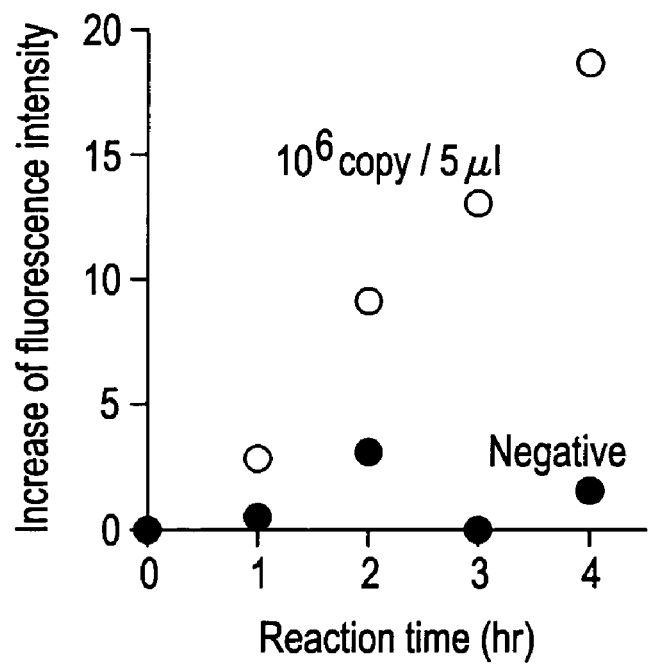

FIG. 13 shows the results of the fluorescence measurement after various times of reactions using the standard RNA ($10^6$ copies/5 μl) in the presence of the fourth single-stranded oligo DNA having a modified 3' end (having ddTTP at the 3' end) in Example 11.

Figure 14:
Figure 15:
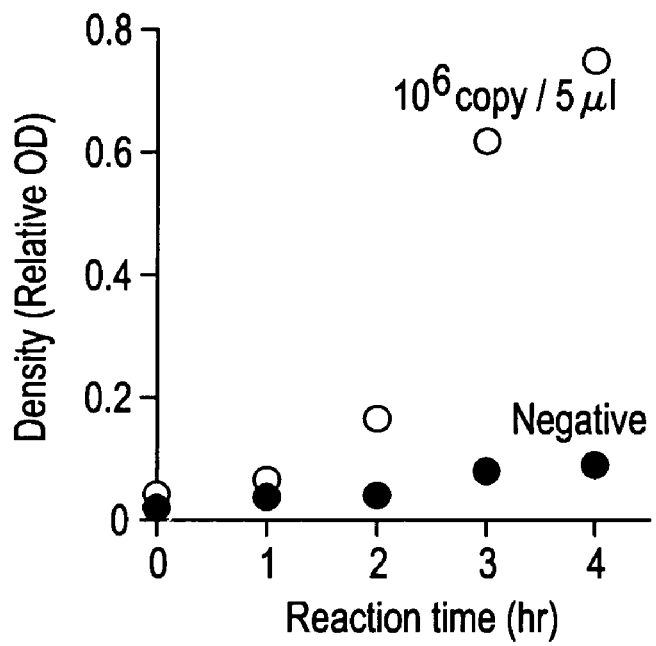

FIG. 14 shows the results of the 2% agarose gel electrophoresis after after various times of reactions using the standard RNA ($10^6$ copies/5 μl) in the presence of the fourth single-stranded oligo DNA having a modified 3' end (having ddTTP at the 3' end) in Example 12.
N: Negative
6: $10^6$ copy/5 μl, initial copy number of standard DNA
C: $10^{11}$ copy/l lane standard DNA
S: φx174/HaeIII FIG. 15 shows the results of the densitometric quantitative analysis of the electrophoretogram shown in FIG. 14 in Example 12.

Figure 16:
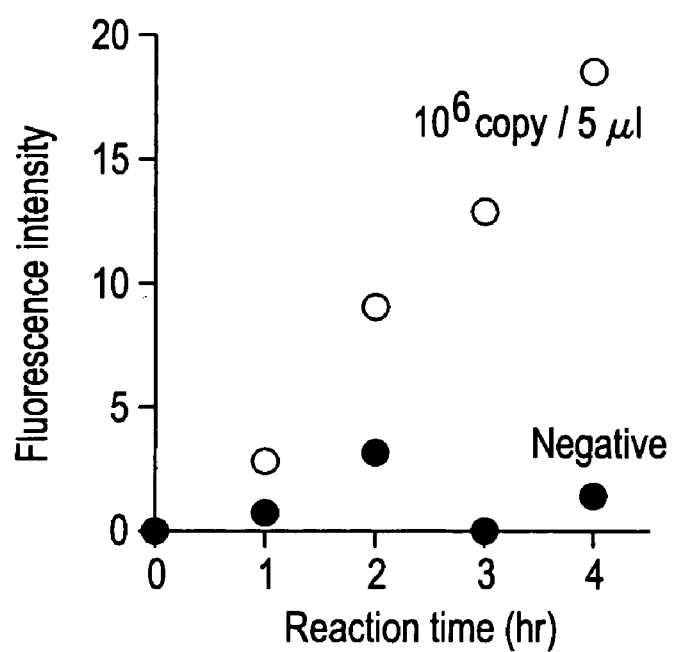

FIG. 16 shows the results of the fluorescence measurement after various times of reactions using the standard RNA ($10^6$ copies/5 μl) in the presence of the fourth single-stranded oligo DNA having a modified 3' end (having ddTTP at the 3' end) in Example 13.

Figure 17:
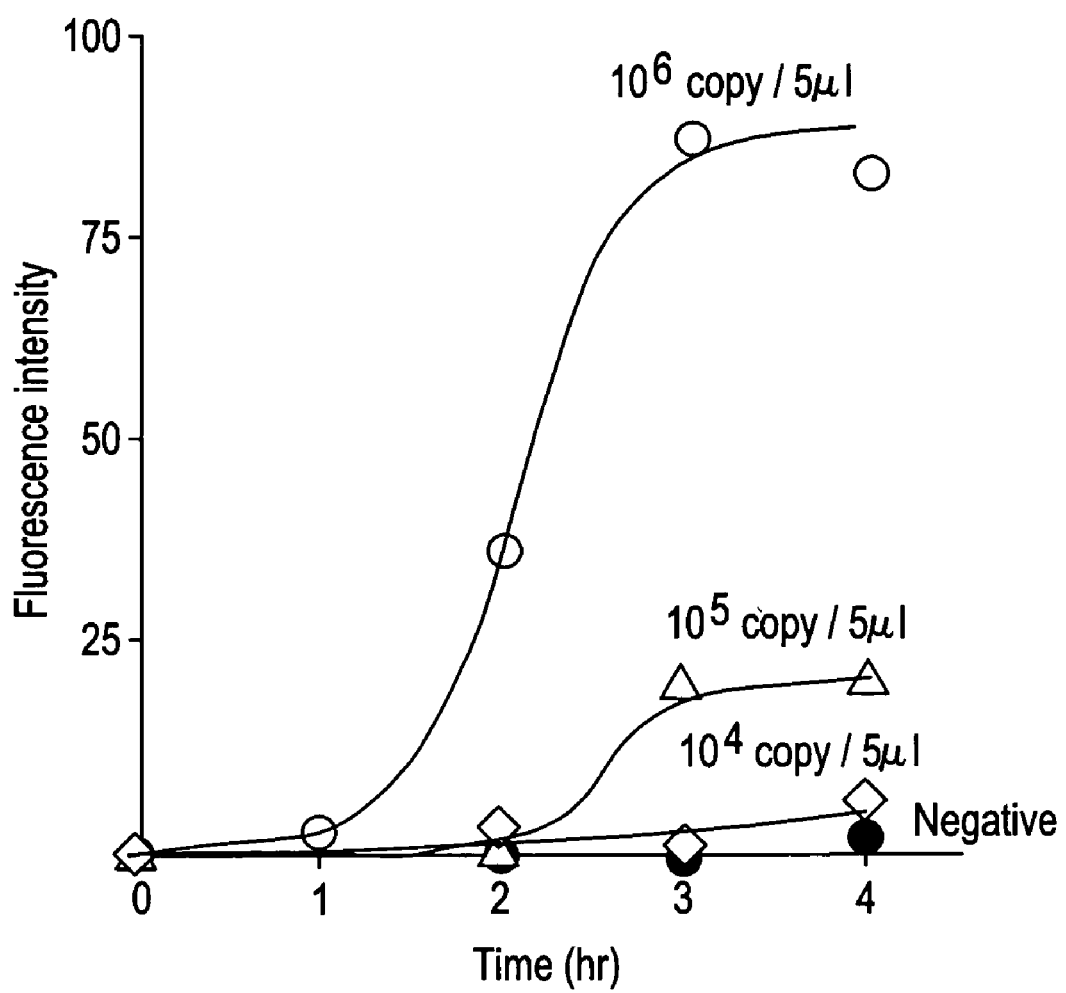

FIG. 17 shows the results of the fluorescence measurement after various times of reactions using the standard RNA ($10^4$, $10^5$ and $10^6$ copies/5 μl) in the presence of the fourth single-stranded oligo DNA having a modified 3' end (having ddTTP at the 3' end) in Example 14.

Figure 18:
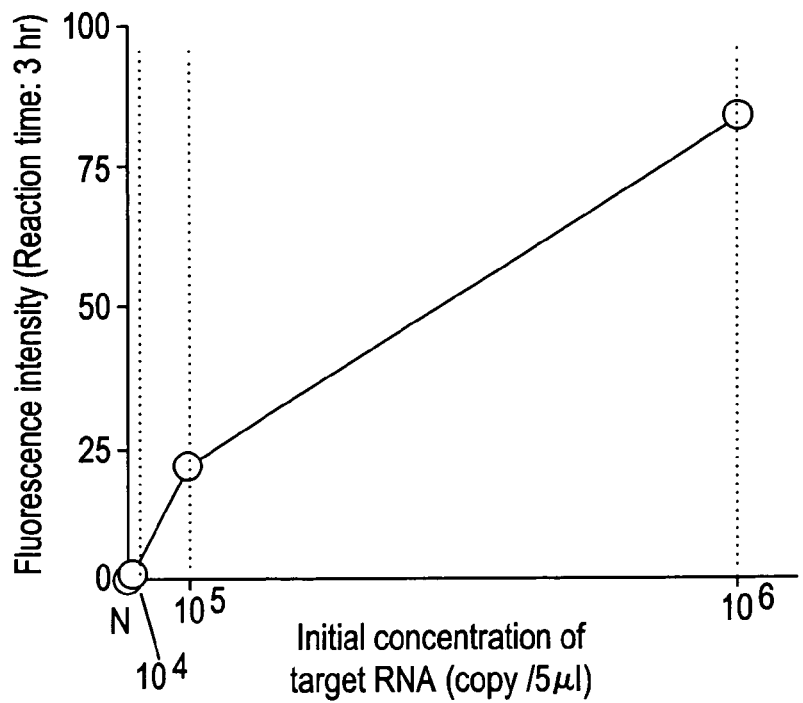

FIG. 18 shows the plot of the fluorescence enhancement at a reaction time of 3 hours against the initial concentration of the standard RNA based on the amplification profiles shown FIG. 17 obtained in Example 14.

Figure 19:
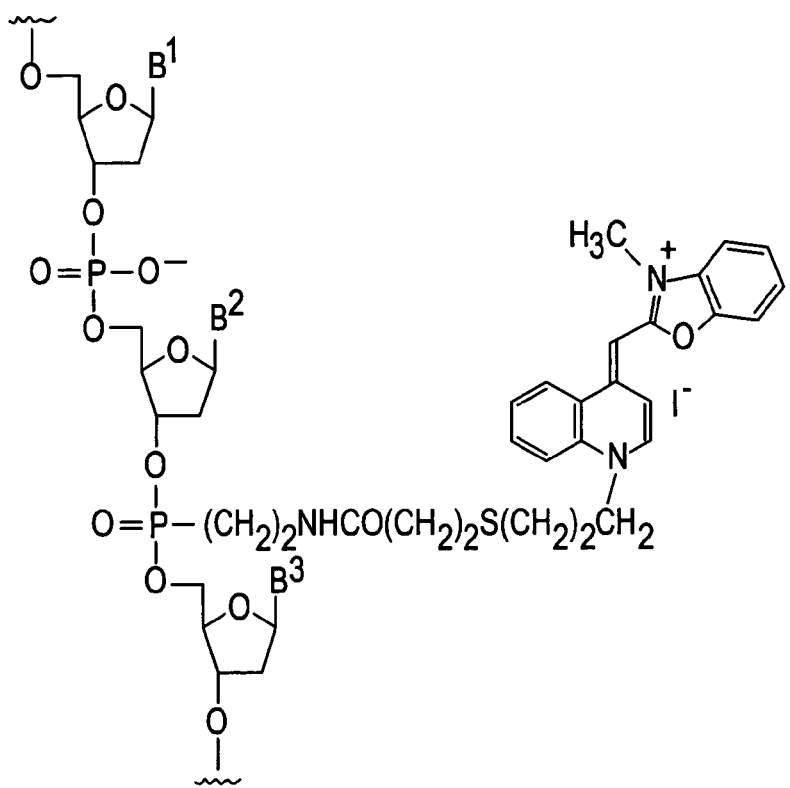

FIG. 19 shows the structure of the fourth single-stranded oligo DNA used in Examples, Yo-271. The DNA moiety on the left and the fluorescent intercalative dye, oxazole yellow on the right are linked via the linker shown in this figure so that the fluorescent dye can intercalates into a double strand upon formation of the double strand by the DNA moiety.

Now, the present invention will be described in detail.

According to Claim 1 of the present application, the present invention provides a method for assay of a single-stranded RNA containing a specific nucleic acids sequence in a sample (a target RNA). Herein, assay means both qualitative assay of the RNA in a sample and quantitative assay of the RNA in a sample.

The specific nucleic acids sequence means a base sequence within the single-stranded RNA which starts at the 5' end with the sequence (3) in the after-mentioned third single-stranded oligo DNA and end at the 3' end with a sequence complementary to the after-mentioned second single-stranded oligo DNA. The specific nucleic acids sequence can be defined arbitrarily but must contain a sequence specific enough to distinguish the target RNA from other nucleic acids. In particular, when a sequence sufficiently distinguishable from nucleic acids other than the target nucleic acid by its 5' and 3' ends is selected as the specific nucleic acids sequence, the specificity of the synthesis of a single-stranded RNA having the specific nucleic acids sequence according to the present invention improves.

Further, when the specific nucleic acids sequence further contains an internal sequence which sufficiently distinguishes the target nucleic acid from other nucleic acids, the specificity of the assay according to the present invention further improves.

In the present invention according to Claim 1, when the target RNA is present in the sample, a large amount of an RNA having the specific nucleic acids sequence is synthesized eventually.

The reagent (A) is a first oligonucleic acid complementary to a neighboring sequence at the 5' end of the specific nucleic acids sequence within the target RNA. The reagent allows the target RNA to be cut at the 5' end of the specific nucleic acids sequence so that on binding of a second single-stranded oligo DNA to the target RNA, an RNA-dependent DNA polymerase synthesizes cDNA from the resulting RNA fragment having the specific nucleic acids sequence at the 5' end as the template in the presence of the after-mentioned reagents (B) to (D) to give a cDNA having a 3'-end sequence complementary to the specific nucleic acids sequence. For example, when a DNA as the first oligonucleic acid is added together with RNase H, the target RNA is cut where the first oligonucleic acid binds to the target RNA, so as to have the first base of the specific nucleic acids sequence at the 5' end. Otherwise, a DNAzyme or ribozyme which catalytically cuts a single-stranded nucleic acid at a specific site (Proc. Natl. Acad. Sci. USA, 94, 4262–4266(1997)) may be used as the first oligonucleic acid.

RNase H non-specifically cleaves an RNA in an RNA-DNA hetero-duplex. Therefore, when RNase H is used, the RNase H is virtually deactivated, for example, by heating or by addition of a known RNase H inhibitor prior to addition of the reagent (B). In the case of heating, it is satisfactory to raise the temperature to 60–70° C. and keep that temperature for quite a short time. Accordingly, when RNase H is used, after the reagent (A) and RNase H are added separately or simultaneously, an appropriate time of incubation precedes addition of the reagents (B) to (I). However, a DNAzyme or a ribozyme as the reagent (A) can be added alone or at the same time as other reagents without the need of heating or addition of an inhibitor.

The reagent (B) is a second single-stranded oligo DNA complementary to a 3'-end sequence within the specific nucleic acids sequence. The reagent (B) hybridizes with the target RNA so that an RNA-dependent DNA polymerase synthesizes cDNA from the RNA as the template in the presence of the after-mentioned reagents (C) to (D) to give a cDNA having a 5'-end sequence complementary to a 3'-end sequence within the specific nucleic acids sequence. The second oligonucleic acid is added in an amount of 0.02 to 1 μM in the presence of the target nucleic acid.

The reagent (C) is an RNA-dependent DNA polymerase, and the reagent (D) is the substrate of the reagent (C), deoxyribonucleoside triphosphates. In the presence of the reagents (B) to (D), a cDNA having a 5'-end sequence complementary to the 3' end of the specific nucleic acids sequence within the target RNA is synthesized.

To the cDNA in the form of a DNA-RNA double strand with the template RNA, the ability to hybridize with a third single-stranded oligo DNA as the after-mentioned reagent (E) is imparted. For this purpose, for example, 5 to 20% of dimethyl sulfoxide (hereinafter referred to as DMSO) is added to make the complementary binding between the DNA and RNA less tight. DMSO does not interfere with the actions of the other reagents and acts satisfactory only if it is added so as to coexist with the DNA-RNA double strand at least prior the DNA synthesis by the reagents (D) to (F). Alternatively, because some RNA-dependent DNA polymerases represented by avian myoblastoma virus polymerase (hereinafter AMV reverse transcriptase) cut RNA in a DNA-RNA double strand, though with low activities, such an enzyme with an RNA degrading action can be used as the above-mentioned reagent (C). It is particularly preferable to use the action of DNSO and the action of an RNA-dependent DNA polymerase such as CMV reverse transcriptase, although it is satisfactory to use the action of either one. By the actions of DMSO and/or an RNA-dependent DNA polymerase, the RNA in the RNA-DNA double strand is degraded and/or separated, leaving a single-stranded DNA.

The reagent (E) is a third single-stranded oligo DNA having (1) a promoter sequence for a DNA-dependent RNA polymerase, (2) an enhancer sequence for the promoter and (3) a 5'-end sequence within the specific nucleic acids sequence in this order from the 5' end. The third oligo DNA is added in an amount of 0.02 to 1 µM in the presence of the target nucleic acid. The region (3) in the third oligo DNA binds to the 3' end of the DNA synthesized in the presence of the reagents (B) to (D). Therefore, in the presence of the reagents (D) and (F), a DNA-dependent DNA polymerase complementarily elongates the 3' end of the third DNA using the DNA as the template and the 3' end of the DNA by using the third oligo DNA as the template to give a complete double-stranded DNA.

The reagent (F) is a DNA-dependent DNA polymerase. In the present invention, it is particularly preferred to use fewer kinds of reagents by using a single enzyme which acts both as the RNA-dependent DNA polymerase as the reagent (C) and as the DNA-dependent DNA polymerase. For example, AMV reverse transcriptase, which has the activities of the two polymerases, is particularly preferable for use in the present invention because it also degrades the RNA chain in a DNA-RNA double strand as described above and is also commercially available.

The reagent (G) is a DNA-dependent RNA polymerase, and the reagent (H) is the substrate of the reagent (G), ribonucleoside triphosphates. The double-stranded DNA synthesized in the presence of the reagents (D) to (F) has a promoter region for the DNA-dependent RNA polymerase at one end. Therefore, in the presence of the reagents (G) and (H), the synthesis of the DNA is immediately followed by synthesis of a single-stranded RNA having the specific nucleic acids sequence. Specific examples of the DNA-dependent RNA polymerase as the reagent (G) include T7 RNA polymerase, T3 polymerase and SP6 RNA polymerase.

The single-stranded RNA synthesized in the presence of the reagents (G) to (H) has the specific nucleic acids sequence. Therefore, coexistence of the synthesized single-stranded RNA with the reagents (B) to (F) sets off the above-mentioned series of reactions again from the start. Thus, in the present invention, it is possible to synthesize above-mentioned double-stranded DNA having a promoter region at one end from a trace of the target RNA in the sample only by adding the respective reagents to the sample without any hardly automatable operations such as heating, and the double-stranded DNA gives rise to synthesis of a single-stranded RNA having the specific nucleic acids sequence. The synthesized single-stranded RNA participates in the next round of synthesis of the double-stranded DNA. Consequently, the single-stranded RNA having the specific nucleic acids sequence drastically increases with the elapse of time.

The rate of synthesis of the single-stranded RNA having the specific nucleic acids sequence and the final amount of the synthesized single-stranded RNA depend on the amount of the target RNA in the sample. Accordingly, the use of the reagent (I) in the present invention enables determination of the target RNA in the sample.

The reagent (I) is a fourth single-stranded labeled oligo DNA containing the sequence complementary to the specific nucleic acids sequence which gives a measurable fluorescent signal on hybridization with a nucleic acid containing the specific nucleic acids sequence. The fourth oligo DNA may be, for example, a fluorescent intercalative dye-linked DNA. The DNA moiety is from 6 to 100 nucleotides long, preferably from 10 to 30 nucleotides long, to secure the specificity for the specific nucleic acids sequence in the assay. Of course, the DNA moiety must be complementary to a sequence within the specific nucleic acids sequence which sufficiently distinguishes the target nucleic acid from other nucleic acids.

The DNA moiety preferably has a 3'-end sequence which is uncomplementary to the specific nucleic acids sequence or has a chemically modified 3' end so that the 3' end does not elongate by the action of the already existing RNA-dependent DNA polymerase on hybridization with the synthesized single-stranded RNA having the specific nucleic acids sequence.

If the DNA moiety is hybridized with another nucleic acid, the fluorescent intercalative dye intercalates into the resulting double strand and changes its fluorescence characteristic. For this purpose, the fluorescent intercalative dye may be linked to the DNA moiety via a linker of an appropriate length. Any linker that does not hinder the fluorescent intercalative dye from intercalating into the double strand may be used without any particular restriction. A bifunctional hydrocarbon linker having functional groups at both ends is particularly preferable for the easiness of its use in modification of oligonucleotides. Alternatively, a commercial kit (C6-Thiolmodifier, tradename, Clonntech) may be used.

The fluorescent intercalative dye is not particularly limited as long as it changes the fluorescent characteristic, for example emits fluorescence having a different peak wavelength, on intercalation into a double strand. However, those which enhance the fluorescence on intercalation are particularly preferable in view of the easiness of fluorescence measurement. More specifically, particularly preferable fluorescent intercalative dyes are, for example, thiazole orange, oxazole yellow and their derivatives, because they show radical change in the fluorescence.

The fluorescent intercalative dye may be linked to any sites of the DNA moiety, including the 5' end, the 3' end and the middle, as long as the linkage neither hinders the fluorescent intercalative dye from intercalating into a double strand nor hinders the DNA moiety from hybridizing with RNA.

The reagent (I) gives off a measurable fluorescent signal in the presence of the single-stranded RNA having the specific nucleic acids sequence synthesized in the presence of the double-stranded DNA, the reagents (G) and (H). Surprisingly, the synthesized single-stranded RNA has been found to serve as a template for DNA synthesis in the presence of the reagents (B) to (D) even when the hybrid of the RNA and the fourth oligo DNA is giving off a fluorescent signal. In other words, in the present invention, a series of events, synthesis of DNA from RNA, synthesis of double-stranded DNA and synthesis of RNA from double-stranded DNA in the presence of the respective reagents, take place in the presence of the fourth oligo DNA.

Therefore, the target nucleic acid in a sample can be determined by measuring the fluorescent signal from the reagent (I) which is added after addition of the reagents (A) to (H) at least once. The reagent (I) may be added at the same time as the other reagents because the presence of the fourth oligonucleic acid is not an obstacle to synthesis of a single-stranded RNA having the specific nucleic acids sequence after all.

When the fluorescent signal is measured only once, prior to the measurement, addition of the reagents (A) to (H) is followed by sufficient time of incubation for synthesis of the single-stranded RNA having the specific nucleic acids sequence. The reagent (I) must be added before the measurement, for example, at the same time as the other reagents. This style of measurement is called an end point assay, and the target nucleic acid in a sample can be determined, for example, from comparison with the results obtained by performing the same procedure on solutions containing the known amounts of the target nucleic acid. In the present invention, the addition of the reagents (A) to (H) is preferably followed by durational measurement of fluorescent signals immediately or after a certain time lag. Though during synthesis of the single-stranded RNA, the fourth DNA binds to and separates from the synthesized RNA repeatedly, but it is possible to monitor the increase of the single-stranded RNA because the measured fluorescent signals from the bound fourth DNA correlate with the amounts of the RNA at the moments of the measurements. The measurement may be done continuously or intermittently at constant intervals. Thus, the time course of the fluorescent signal can be traced by durational measurement, and the amount (initial amount) of the target RNA in a sample can be determined, for example, from the time required to obtain a stable fluorescent signal after addition of the reagents (A) to (H) or the time lag between the addition of the reagents (A) to (H) and drastic increase of the fluorescent signal.

As will be demonstrated later in Examples, in the present invention, all the above-mentioned reagents (A) to (I) are preferred to be free from chlorides. Further, it is preferred to use an acetate such as magnesium acetate or potassium acetate in addition to the reagents (A) to (H). An acetate is added at latest at the time of synthesis of single-stranded DNA in the presence of the reagents (B) to (D) preferably at a concentration of from 5 to 20 mM for magnesium acetate, from 50 to 200 mM for potassium acetate. In the present invention, it is preferred to further use sorbitol. Sorbitol is added at latest at the time of synthesis of single-stranded DNA in the presence of the reagents (B) to (D). Further, use of protein such as bovine serum albumin and a reducing agent such as dithiothreitol, use of an RNase inhibitor with a view to inhibiting degradation of the synthesized single-stranded RNA by RNase are also preferred. Still further, a buffering agent is also preferably used so as to keep the reaction solution within an active pH range for the respective enzymes to be used. As the buffering agent, tris-acetate is particularly preferable. These reagents are added at latest at the time of synthesis of single-stranded DNA in the presence of the reagents (B) to (D). Use of these optional reagents leads to increase of the amount of the single-stranded RNA synthesized as the product.

The method of the present invention enables assay of a target RNA in a sample at constant temperature without heating. The constant temperature is may be any temperature at which the respective oligonucleic acids used as the reagents (A), (B), (E) and (I) in the present invention can hybridize, and the enzymes as the reagents (C), (F) and (F) are active, without any restriction. Specifically speaking, the temperature is selected from the range of from 35 to 60° C. The temperature may not be exactly constant, and it is sufficient to keep the temperature almost constant.

As is evident from the above explanation, in the assay method according to Claim 1, the reagents to be used may be added one by one, in combination of at least two or all at once. In particular, when all the reagents are added to a sample all at once, assay of the target RNA in a closed vessel can be realized to solve the problem of carryover of the synthesized single-stranded RNA which can happen when the vessel is opened or closed.

According to Claim 21 of the present application, the present invention provides a simple method for producing a nucleic acid having a specific nucleic acids sequence at almost constant temperature by using at least the following reagents (A) to (G), which comprises a step of adding the reagents (A) to (G) one by one (in any order), in combinations of at least two or all at once to a single-stranded DNA having (1) a promoter sequence for a DNA-dependent RNA polymerase, (2) an enhancer sequence for the promoter and (3) the specific nucleic acids sequence in this order from the 5' end or to a double-stranded DNA consisting of the single-stranded DNA and a complementary DNA and a step of measuring a fluorescent signal from the reagent (H) at least once in the presence of at least the reagents (A) to (G);

(A) a single-stranded oligo DNA complementary to a 3'-end sequence in the specific nucleic acids sequence,
(B) an RNA-dependent DNA polymerase,
(C) a DNA-dependent DNA polymerase,
(D) a deoxyribonucleoside triphosphate,
(E) a DNA-dependent RNA polymerase,
(F) a ribonucleoside triphosphate,
(G) a single-stranded DNA having (1) a promoter sequence for a DNA-dependent RNA polymerase, (2) an enhancer sequence for the promoter and (3) a 5'-end sequence in the specific nucleic acids sequence in this order from the 5' end,
(H) a fourth single-stranded labeled oligo DNA containing the sequence complementary to the specific nucleic acids sequence which gives a measurable fluorescent signal on hybridization with a nucleic acid containing the specific nucleic acids sequence.

As is understandable from the explanation already made, in the method according to Claim 23, a nucleic acid having a specific nucleic acids sequence is produced by using the double-stranded DNA from which the single-stranded RNA is synthesized in the method according to Claim 1, as the starting material. The specific nucleic acids sequence used herein does not have to be attributed to the target RNA, unlike the specific nucleic acids sequence in Claim 1.

The double-stranded DNA as the starting material can be prepared by known methods using PCR or a DNA synthesizer. The first oligo DNA as the reagent (A) hybridizes with the single-stranded DNA having (1) a promoter sequence for a DNA-dependent RNA polymerase, (2) an enhancer sequence for the promoter and (3) the specific nucleic acids sequence and elongates using the DNA as the template in the presence of the reagents (A), (C) and (D) to give the double-stranded DNA, which serves as the starting material. The double-stranded DNA as the starting material can also be prepared by performing the respective operations mentioned for the method according to Claim 1 on a single-stranded RNA containing the specific nucleic acids sequence. The single-stranded DNA as the reagent (A), the single-stranded oligo DNA as the reagent (G) and the single-stranded oligo DNA as the reagent (H) correspond to the second oligo DNA, the third oligo DNA and the fourth oligo DNA in the method according to Claim 1. Therefore, the modes of addition and actions of these reagents, preferable examples of the respective polymerases, optional reagents other than (A) to (H) and the procedure can be easily understandable by referring to the previous explanation. In short, a single-stranded RNA having the specific nucleic acids sequence is synthesized from the double-stranded DNA as the starting material in the presence of the reagents (E) and (F), then from the single-stranded RNA a single-stranded DNA complementary to the specific nucleic acids sequence is synthesized in the presence of the reagents (E) and (F), and from the single-stranded DNA the double-stranded DNA as the starting material is synthesized in the presence of the reagents (C) and (D). In this method, the reagent (A) used in the method according to Claim 1 and the operations associated with the reagent (A) such as heating are unnecessary in this method unless the double-stranded DNA as the starting material is prepared from a single-stranded RNA which containing the specific nucleic acids sequence somewhere other than the 5' end.

When the fluorescent signal is measured only at once, the measurement is done in the presence of the reagent (I) after sufficient time of incubation following the addition of the reagents (A) to (G). When the fluorescent signal is measured over a period of time, the durational measurement follows addition of the reagents (A) to (G) immediately or after a certain time lag. Once production of a predetermined amount of a nucleic acid having the specific nucleic acids sequence is indicated by the measured fluorescent signal or the time course of the fluorescent signal, then the produced nucleic acid is extracted.

To obtain a single-stranded RNA having the specific nucleic acids sequence as the final product, RNA extraction is preceded by addition of an enzyme which degrades DNA such as DNase. To obtain a single-stranded DNA containing the specific nucleic acids sequence or a double-stranded DNA consisting of such a DNA single strand and a complementary strand as the final product, DNA extraction is preceded by addition of an enzyme which degrades RNA such as RNase. Of course, a mixture of such an RNA and such a DNA can be obtained by extraction without addition of a nuclease. DNA and/or RNA can be easily extracted by known techniques such as ethanol precipitation.

The present invention according to Claim 1 or 21 described above can be performed, for example, by using a reagent set which comprises at least a first reagent containing a first single-stranded oligonucleic acid, a second reagent containing tris-acetate, magnesium acetate, potassium acetate, sorbitol and dimethyl sulfoxide, a third reagent containing dithiothreitol, deoxyribonucleoside triphosphates, ribonucleoside triphosphates, bovine serum albumin, a second single-stranded oligo DNA and a third single-stranded oligo DNA, a fourth reagent containing an RNA-dependent DNA polymerase, a DNA-dependent DNA polymerase, a DNA-dependent RNA polymerase and an RNase inhibitor and a fifth reagent containing a fourth single-stranded oligo DNA, and by adding these reagents in numerical order to a sample. When the present invention according to Claim 21 does not require the first single-stranded oligonucleic acid, the first reagent can be omitted.

The present invention according to Claim 1 or 21 described above can also be performed, for example, by using a reagent set which comprises at least a first reagent containing a first single-stranded oligonucleic acid, a second reagent containing tris-acetate, magnesium acetate, potassium acetate, sorbitol and dimethyl sulfoxide, a third reagent containing dithiothreitol, deoxyribonucleoside triphosphates, ribonucleoside triphosphates, bovine serum albumin, a second single-stranded oligo DNA, a third single-stranded oligo DNA and a fourth single-stranded oligo DNA and a fourth reagent containing an RNA-dependent DNA polymerase, a DNA-dependent DNA polymerase, a DNA-dependent RNA polymerase and an RNase inhibitor, and by adding these reagents in numerical order to a sample. When the present invention according to Claim 21 does not require the first single-stranded oligonucleic acid, the first reagent can be omitted.

The present invention according to Claim 1 or 21 described above can also be performed, for example, by using a reagent set which comprises at least a first reagent containing a first single-stranded oligonucleic acid, a second reagent containing tris-acetate, magnesium acetate, potassium acetate, sorbitol and dimethyl sulfoxide, a third reagent containing dithiothreitol, deoxyribonucleoside triphosphates, ribonucleoside triphosphates, bovine serum albumin, a second single-stranded oligo DNA and a third single-stranded oligo DNA, a fourth reagent containing a fourth single-stranded oligo DNA, an RNA-dependent DNA polymerase, a DNA-dependent DNA polymerase, a DNA-dependent RNA polymerase and an RNase inhibitor, and by adding these reagents in numerical order to a sample. When the present invention according to Claim 21 does not require the first single-stranded oligonucleic acid, the first reagent can be omitted.

The present invention according to Claim 1 or 21 described above can also be performed, for example, by using a reagent which comprises at least a first single-stranded oligonucleic acid, a second single-stranded oligo DNA, a third single-stranded oligo DNA, a fourth single-stranded oligo DNA, an RNA-dependent DNA polymerase, a DNA-dependent DNA polymerase, a DNA-dependent RNA polymerase, deoxyribonucleoside triphosphates, ribonucleoside triphosphates, tris-acetate, magnesium acetate, potassium acetate, sorbitol, dimethyl sulfoxide, dithiothreitol, bovine serum albumin and an RNase inhibitor, and by adding the reagent to a sample. When the present invention according to Claim 21 does not require the first single-stranded oligonucleic acid, the first single-stranded oligo DNA can be omitted. The reagent is a single reagent containing all the required constituents, unlike the other reagent sets. Therefore, it works satisfactory when added to a sample only once.

The concentration of each constituent in the above-mentioned reagent sets or reagent should be adjusted so that each constituent is present in an required amount in a sample when added to the sample. As described previously, a single enzyme having the actions of both RNA-dependent DNA polymerase and DNA-dependent DNA polymerase may be used as the RNA-dependent DNA polymerase and DNA-dependent DNA polymerase.

Now, the present invention will be described in further detail by referring to Examples. However, the present invention should be by no means is restricted to these specific Examples.

EXAMPLE 1

Preparation Of Double-stranded DNA

A double-stranded DNA consisting of a DNA single strand having the SP6 promoter sequence at the 5' end and a complementary DNA single strand, was prepared.

70 µl of a reaction solution having the following composition was pored into a PCR tube.
  10.7 mM tris-HCl buffer (pH 8.3)
  53.6 mM potassium chloride
  2.36 mM magnesium chloride
  0.268 mM each of dATP, dGTP, dCTP and dTTP
  0.257 µM third single-stranded oligo DNA (sequence) 5' ATT TAG GTG ACA CTA TAG AAT ACA ACA CTC CAC CAT AGA TCA CTC CCC TG 3' (SEQ ID NO:1)
  0.257 µM second single-stranded oligo DNA (sequence) 5' ACT CGC AAG CAC CCT ATC A 3' (SEQ ID NO:2)
  0.032 U/µl commercially available DNA-dependent DNA polymerase (Ampli Taq, tradename, Perkin Elmer)

Then, 5 µl of a 1,865-bp double-stranded DNA ($10^{-6}$ copies) containing bases 1 to 1,863 in human hepatitis C virus (HCV) cDNA was added as a standard DNA. For the base numbers, literature (Kato et al,. Proc. Natl. Sci., USA, 1990, 87, 9524–9528) should be referred to.

Then, the reaction solution was heated and incubated at 95° C. for 9 minutes, and an incubation cycle of the following steps (1) to (3) were repeated 40 times.
  (1) Incubation at 95° C. for 30 seconds,
  (2) Incubation at 65° C. for 30 seconds and
  (3) Incubation at 72° C. for 1 minute.

After 40 cycles of incubation, the reaction solution was withdrawn and subjected to 2% agarose electrophoresis followed by ethidium bromide staining.

Figure 1:
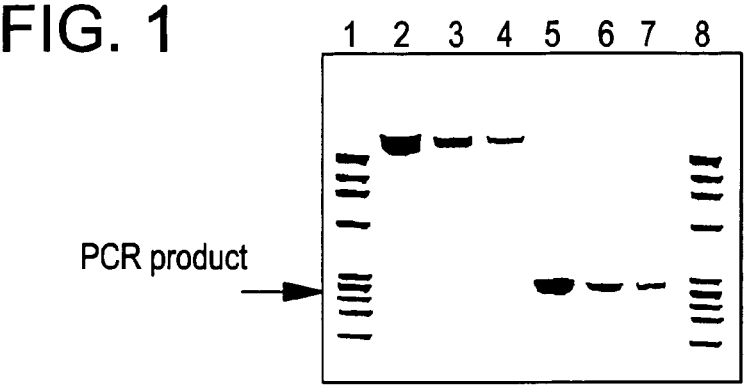

FIG. 1 shows the results on the gel stained with ethidium bromide. FIG. 1 clearly shows single bands of DNA of about 320 bp., indicating that preparation of a DNA having the following base sequence containing the SP6 promoter sequence (underlined) at the 5' end and a complementary strand by the above-mentioned procedure.

(sequence) 5' ATT TAG GTG ACA CTA TAG AAT ACA A-(bases 11 to 300 in HCV cDNA) 3' (nucleotides 1–25 of SEQ ID NO:6)

EXAMPLE 2

Effects of Magnesium Acetate Concentration

The optimum concentration of magnesium acetate for the present invention was studied. Reaction solutions having the following composition were prepared, and 14 µl of the reaction solutions were pored into PCR tubes.
  85.7 mM tris-acetate (pH 8.1)
  16.1, 32.1 or 48.2 mM magnesium acetate
  214.3 mM potassium acetate
  21.4% DMSO
  32.1% sorbitol
  2.1 mM each of ATP, GTP, CTP and UTP
  2.1 mM each of dATP, dGTP, dCTP and dTTP
  214 µg/ml BSA
  0.12 mM second single-stranded oligo DNA
  (sequence) 5' ACT CGC AAG CAC CCT ATC A 3'(SEQ ID NO:2)

Then, 10 µl of a standard DNA ($10^4$ copies, $10^5$ copies, $10^6$ copies and $10^7$ copies/10 µl) or 10 µl of DNA-free TE buffer (10 mM tris-HCl (pH 8.0) containing 0.1 mM EDTA) as a negative control was added. The standard DNA was a double-stranded DNA consisting of a DNA strand having the following sequence and a complementary DNA strand.

(sequence) 5' ATT TAG GTG ACA CTA TAG AAT ACA A-(bases 11 to 300 in HCV cDNA) 3' (nucleotides 1–25 of SEQ ID NO:6)

The reaction solutions were overlaid with 100 µl mineral oil and incubated at 45° C. for 5 minutes. Subsequently, 5 µl of a mixed solution of the following enzymes was added, and reaction was carried out at 45° C. for 1 hour.
  30 U/µl commercially available SP6 RNA polymerase (Takara Shuzo Co., Ltd.)
  12 U/µl commercially available RNase inhibitor (Takara Shuzo Co., Ltd.)

Then, 0.6 µl of a third single-stranded oligo DNA (2.75 µM) was added.

(sequence) 5' ATT TAG GTG ACA CTA TAG AAT ACA ACA CTC CAC CAT AGA TCA CTC CCC TG 3' (SEQ ID NO:1)

Subsequently 0.4 µl of AMV reverse transcriptase (37 U/µl, Takara Shuzo Co., Ltd.), as an RNA dependent DNA polymerase and as a DNA-dependent DNA polymerase, was added. After 2 hours of incubation at 45° C., 5 µl of the reaction solutions were subjected 2% agarose gel electrophoresis. After the electrophoresis, the agarose gel was stained with 10,000-fold diluted SYBR Green II (Takara Shuzo Co., Ltd.) for 30 minutes.

Figure 2:
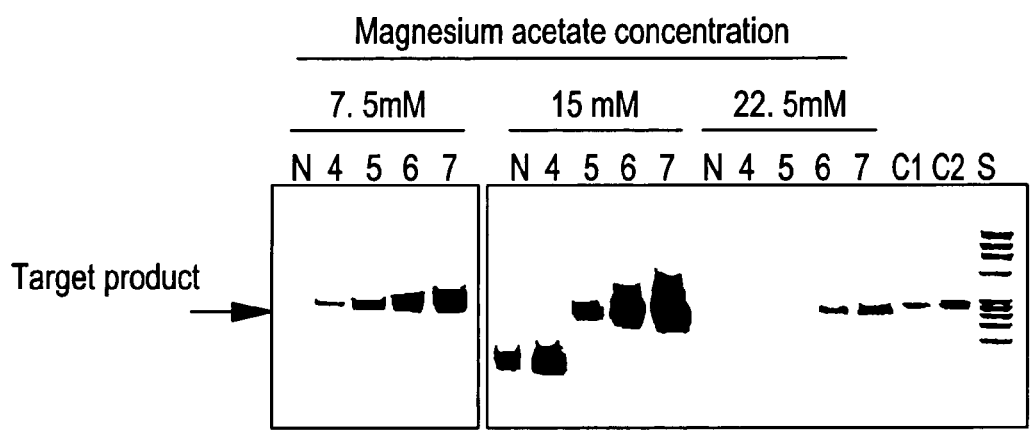

FIG. 2 shows the pattern on the stained gel. A maximal amount of the product was obtained in the presence of magnesium acetate at a final concentration of 15 mM.

EXAMPLE 3

Effects of Potassium Acetate

The optimum concentration of magnesium acetate for the present invention was studied. Reaction solutions having the following composition were prepared, and 14 µl of the reaction solutions were pored into PCR tubes.
  85.7 mM tris-acetate (pH 8.1)
  28.9 mM magnesium acetate
  214.3, 235.7, 257.1 or 278.6 mM potassium acetate
  21.4% DMSO
  32.1% sorbitol
  2.1 mM each of ATP, GTP, CTP and UTP
  2.1 mM each of dATP, dGTP, dCTP and dTTP
  214 µg/ml BSA
  0.12 µM second single-stranded oligo DNA
  (sequence) 5' ACT CGC AAG CAC CCT ATC A 3' (SEQ ID NO:2)

Then, 10 µl of a standard DNA ($10^3$ copies, $10^4$ copies, $10^5$ copies and $10^6$ copies/10 µl) or 10 µl of DNA-free TE buffer (10 mM tris-HCl (pH 8.0) containing 0.1 mM EDTA) as a negative control was added. The standard DNA was a double-stranded DNA consisting of a DNA strand having the following sequence and a complementary DNA strand.

(sequence) 5' ATT TAG GTG ACA CTA TAG AAT ACA A-(bases 11 to 300 in HCV cDNA) 3' (nucleotides 1–25 of SEQ IN NO:6)

The reaction solutions were overlaid with 100 µl mineral oil and incubated at 45° C. for 5 minutes. Subsequently, 5 µl of a mixed solution of the following enzymes was added, and reaction was carried out at 45° C. for 1 hour.

30 U/μl commercially available SP6 RNA polymerase (Takara Shuzo Co., Ltd.)

12 U/μl commercially available RNase inhibitor (Takara Shuzo Co., Ltd.)

Then, 0.6 μl of a third single-stranded oligo DNA (2.75 μM) was added.

(sequence) 5' ATT TAG GTG ACA CTA TAG AAT ACA ACA CTC CAC CAT AGA TCA CTC CCC TG 3' (SEQ ID NO:1)

Subsequently 0.4 μl of AMV reverse transcriptase (37 U/μl, Takara Shuzo Co., Ltd.), as an RNA dependent DNA polymerase and as a DNA-dependent DNA polymerase, was added. After 2 hours of incubation at 45° C., 5 μl of the reaction solutions were subjected 2% agarose gel electrophoresis. After the electrophoresis, the agarose gel was stained with 10,000-fold diluted SYBR Green II (Takara Shuzo Co., Ltd.) for 30 minutes.

Figure 3:
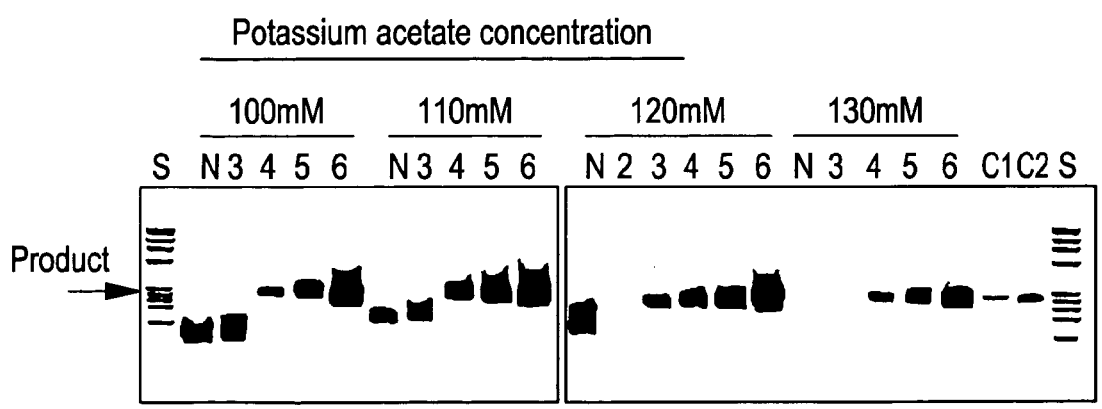
Figure 4:
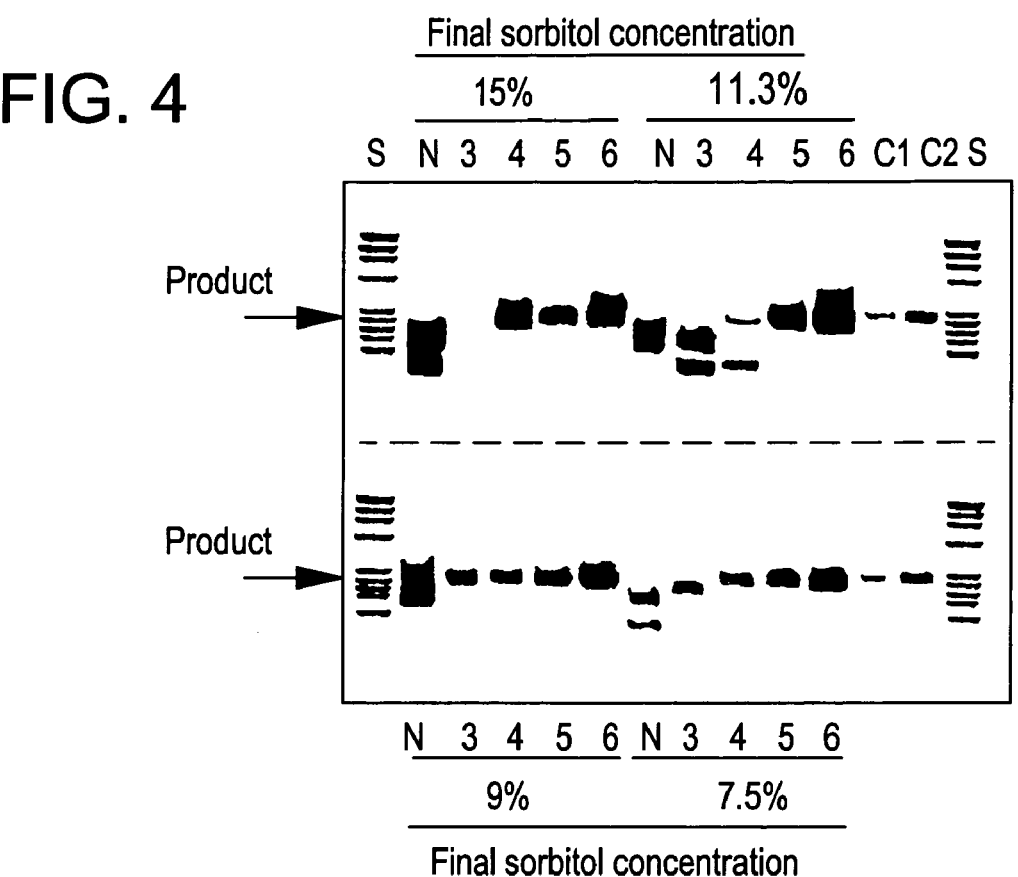

FIG. 3 shows the pattern on the stained gel. Even when the initial copy numbers of the target nucleic acid was $10^3$, the product was obtained in the presence of potassium acetate at a final concentration of 120 mM.

The amount of the amplification product from various concentrations of a double-stranded DNA as the target nucleic acid was studied. A reaction solution having the following composition was prepared, and 19 μl of the reaction solution was poured into PCR tubes.

63.2 mM tris-acetate (pH 8.1)
21.3 mM magnesium acetate
197.4 mM potassium acetate
22.5% DMSO
22.5% sorbitol
1.6 mM each of ATP, GTP, CTP and UTP
1.6 mM each of dATP, dGTP, dCTP and dTTP
157.9 μg/ml BSA
0.055 μM second single-stranded oligo DNA
(sequence) 5' ACT CGC AAG CAC CCT ATC A 3' (SEQ ID NO:2)

Then, 5 μl of a standard DNA ($10^3$ copies, $10^4$ copies, $10^5$ copies or $10^6$ copies/5 μl) or 5 μl of RNA-free TE buffer as a negative control was added. The standard DNA was a double-stranded DNA consisting of a DNA strand having the following sequence and a complementary DNA strand.

(sequence) 5' ATT TAG GTG ACA CTA TAG AAT ACA A-(bases 11 to 300 in HCV cDNA) 3' (nucleotides 1–25 of SEQ ID NO:6)

The reaction solutions were overlaid with 100 μl mineral oil and incubated at 45° C. for 5 minutes. Subsequently, 5 μl of a mixed solution of the following enzymes was added, and reaction was conducted at 45° C. for 1 hour.

30 U/μl commercially available SP6 RNA polymerase (Takara Shuzo Co., Ltd.)

12 U/μl commercially available RNase inhibitor (Takara Shuzo Co., Ltd.)

Then, 2.75 μl of a third single-stranded oligo DNA (2.75 μM) was added.

(sequence) 5' ATT TAG GTG ACA CTA TAG AAT ACA ACA CTC CAC CAT AGA TCA CTC CCC TG 3' (SEQ ID NO:1)

Subsequently, 0.4 μl of AMV reverse transcriptase (37 U/μl, Takara Shuzo Co., Ltd.), as an RNA-dependent DNA polymerase and as a DNA-dependent DNA polymerase, was added. After 2 hours of incubation at 45° C., 5 μl of the reaction solutions were subjected to 2% agarose gel electrophoresis. After the electrophoresis, the agarose gel was stained with 10,000 fold diluted SYBR Green II (Takara Shuzo Co., Ltd.) for 30 minutes.

Figure 5:
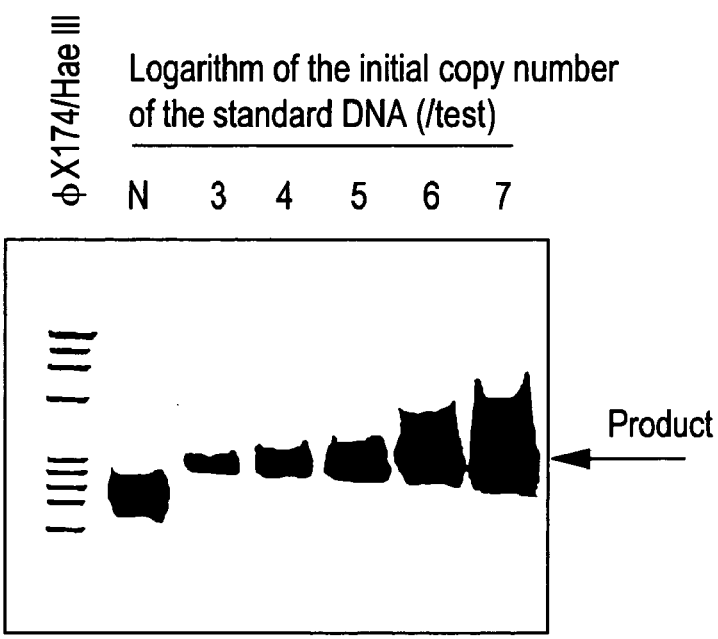

FIG. 5 shows the pattern on the stained gel. Whenever the initial amount of the target nucleic acid was $10^3$ copies/5 μl or more, bands of about 300 bp were detected, and the band density was dependent on the initial amount of the nucleic acid, which indicates the possibility of high sensitivity assay of a double-stranded DNA as the target nucleic acid.

EXAMPLE 6

Specific Cutting of RNA Using First Single-stranded Oligonucleic Acid and RNaseH RNA was cleaved at the 5' end of a specific nucleic acids sequence by using a first single-stranded oligonucleic acid and RNaseH.

A reaction solution having the following composition was prepared, and 7.2 μl of the reaction solution was pored into PCR tubes.

40 mM tris-HCl buffer (pH 8.0)
4 mM magnesium chloride
1 mM dithiothreitol
1 μM first single-stranded oligo DNA (11 mer)
(sequence) 5' GTC GCC CCC AA 3' (SEQ ID NO:3)

Then, 1.8 μl of RNA (133 mer, 5.7 μM) was added, 10 minutes of heating at 65° C. was followed by sudden cooling in ice-cold water. The 133 mer RNA had the following sequence.

(sequence) 5' (vector sequence) GGG AAA GCU UGC AUG CCU GCA GGU CGA CUC UAG AGG AUC CCC GGG UAC CGA GCU CGA AUU CC (sequence from HCV) U UGG GGG CGA CAC UCC ACC AUA GAU CAC UCC CCU GUG AGG AAC UAC UGU CUU CAC GCA GAA AGC GUC UAG C 3' (SEQ ID NO:4)

(The sequence complementary to the 11 mer DNA is underlined.)

After 5 minutes of incubation at 37° C., 1 μl of RNaseH (0.01, 0.001, 0.0001 or 0.00001 U/μl, Takara Shuzo Co., Ltd.) was added, and reaction was conducted at 37° C. for 1 hour. To the reaction solutions, 2 μl gel loading buffer (0.1 M tris-HCl (pH 8.0) containing 60 mM EDTA, 0.25% Bromophenol Blue and 40% sucrose) and then 12 μl formamide were added. After 5 minutes of incubation at 65° C., 12 μl of the reaction solutions were subjected to electrophoresis on a polyacrylamide gel containing 12% urea.

The acrylamide gel was washed with water three times for 5 minutes each time and stained with 10,000-fold diluted SYBR Green II (Takara Shuzo Co., Ltd.) for 30 minutes.

Separately, a reaction solution having the following composition was prepared, and 10.8 μl of the reaction solution was pored into PCR tubes.

40 mM tris-acetate buffer (pH 8.1)
37 mM magnesium acetate
347 mM potassium acetate
22% sorbitol
1 mM dithiothreitol
0.9 μM first single-stranded oligonucleic acid (11 mer)
(sequence) 5' GTC GCC CCC AA 3' (SEQ ID NO:3)

Then, 1.8 μl of RNA (133 mer, 5.7 μM) was added, and 10 minutes of heating at 65° C. was followed by sudden cooling in ice-cold water.

After 5 minutes of incubation at 37° C., 1 μl of RNaseH (0.01, 0.001, 0.0001 or 0.00001 U/μl, Takara Shuzo Co., Ltd.) was added, and reaction was conducted at 37° C. for 1 hour. To the reaction solutions, 2 μl gel loading buffer and then 10 μl formamide were added. After 5 minutes of incubation at 65° C., 12 µl of the reaction solutions were subjected to electrophoresis on a polyacrylamide gel containing 12% urea.

The acrylamide gel was washed with water three times for 5 minutes each time and stained with 10,000-fold diluted SYBR Green II (Takara Shuzo Co., Ltd.) for 30 minutes.

Figure 6:
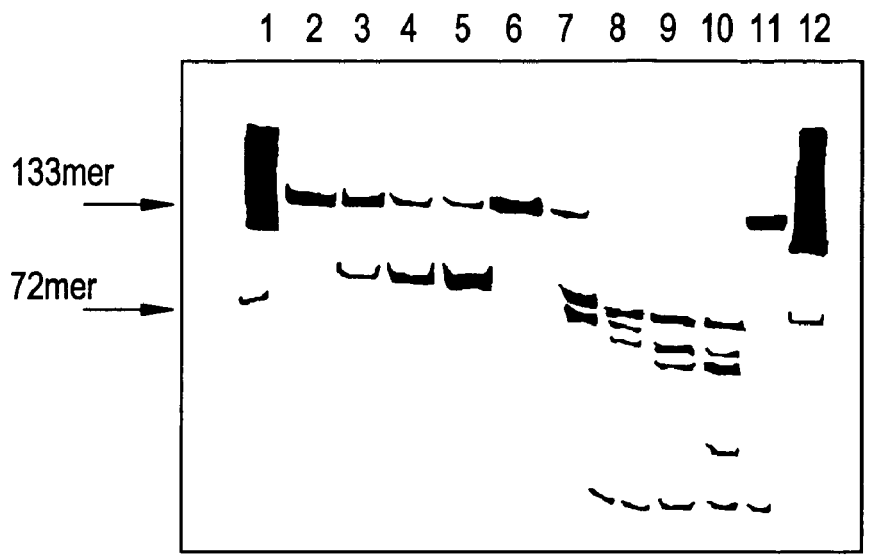

FIG. 6 shows the results obtained in the respective reaction solutions having different compositions. When the tris-HCl buffer was used in the presence of RNaseH at final concentrations of 0.000001 and 0.00001 U/µl, the band of the 133 mer disappeared, and bands of 60 to 70 mers were detected. The still higher final concentration of RNaseH resulted in further degradation of the 133 mer. On the other hand, when the tris-acetate buffer was used in the presence of RNaseH at a final concentration of 0.0007 U/µl, the band of the 133 mer disappeared, and a band of a 60 to 70 mer was detected. This band agrees with the RNA fragment obtained when the 133 mer RNA is cut where the first single-stranded oligonucleic acid binds to the 133 mer in terms of mobility.

Thus it was possible to cut the target RNA at the 5' end of the specific nucleic acids sequence by using the first single-stranded oligonucleic acid and RNaseH.

EXAMPLE 7

Amplification of RNA as Target Nucleic Acid

The present invention was performed by using various concentrations of a target RNA, and the amplification products were examined. A reaction solution having the following composition was prepared, and 20 µl of the reaction solution was pored into PCR tubes.

60 mM tris-acetate (pH 8.1)
20.3 mM magnesium acetate
187.5 mM potassium acetate
22.5% DMSO
22.5% sorbitol
1.5 mM each of ATP, GTP, CTP and UTP
1.5 mM each of dATP, dGTP, dCTP and dTTP
150 µg/ml BSA
0.3 µM third single-stranded oligo DNA
(sequence) 5' ACT TAG GTG ACA CTA TAG AAT ACA ACA CTC CAC CAT AGA TCA CTC CCC TG 3' (SEQ ID NO:1)
0.3 µM second single-stranded oligo DNA
(sequence) 5' ACT CGC AAG CAC CCT ATC A 3' (SEQ ID NO:2)

Then, 5 µl of a standard RNA ($10^2$ copies, $10^3$ copies, $10^4$ copies, $10^5$ copies or $10^6$ copies/5 µl) or 5 µl of RNA-free TE buffer as a negative control was added. The standard RNA had the following sequence.

(sequence) 5' GAA UAC AA-(bases 11 to 300 in HCV RNA) 3' (nucleotides 1–8 of SEQ ID NO:7)

The reaction solutions were overlaid with 100 µl mineral oil and incubated at 65° C. for 10 minutes, and then the tubes were allowed to stand still in ice-cold water for 5 minutes. Then, 5 µl of a mixed solution of the following enzymes was added, and reaction was conducted at 45° C. for 4 hours.

36 U/µl commercially available SP6 RNA polymerase (Takara Shuzo Co., Ltd.)
12 U/µl commercially available RNase inhibitor (Takara Shuzo Co., Ltd.)
9 U/µl AMV reverse transcriptase (Takara Shuzo Co., Ltd.), as an RNA-dependent DNA polymerase and as a DNA-dependent DNA polymerase 5 µl of the reaction solutions were subjected to agarose gel electrophoresis. After the electrophoresis, the agarose gel was stained with 10,000-fold diluted SYBR Green II (Takara Shuzo Co., Ltd.) for 30 minutes.

Figure 7:
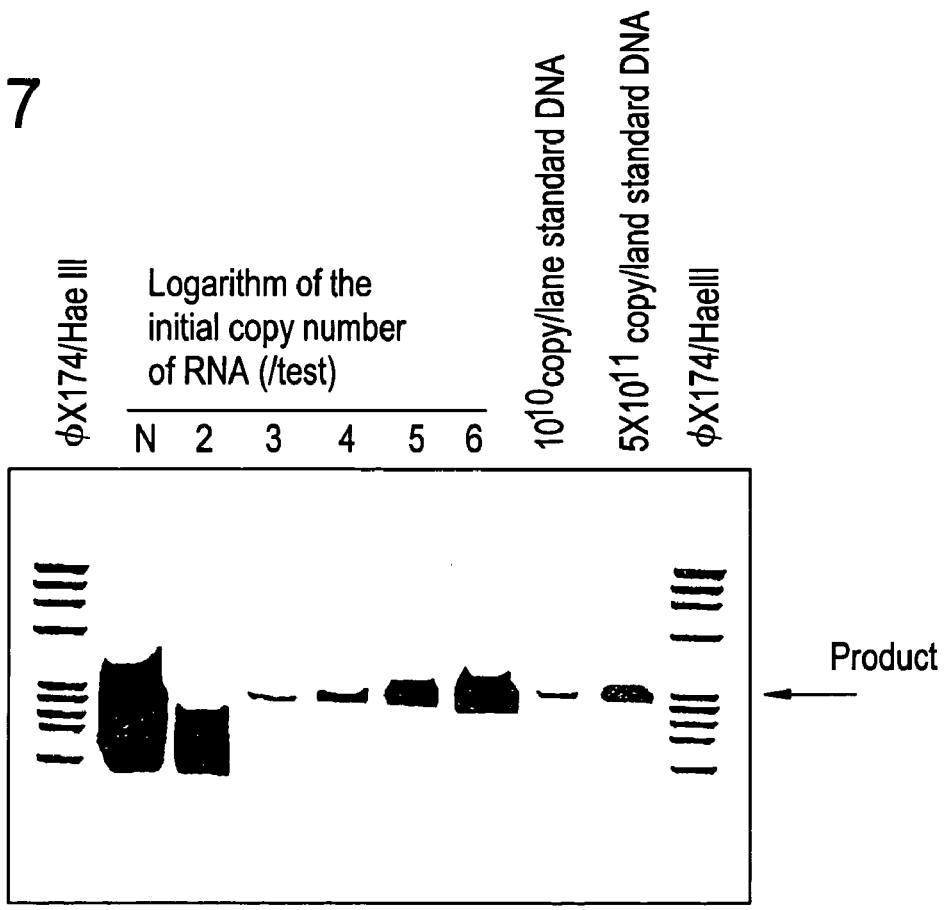

FIG. 7 shows the pattern on the stained gel. As shown in FIG. 7, when the initial concentration of the target RNA was $10^3$ copies/5 µl or more, bands of about 300 bp were detected, and the band density was dependent on the initial amount of the RNA. Thus, it was possible to detect the target RNA with high sensitivity by the present invention. The amount of the amplification product increased with the elapse of time and was dependent on the initial amount of the target RNA.

EXAMPLE 8

Identification of Amplification Product

Amplification products was identified after treatment with DNase or RNase. The procedure in Example 7 was followed until the use of the enzymes in 5 µl of TE buffer as a negative control and in 5 µl of a standard RNA ($10_5$ copies or $10_6$ copies/5 µl). The standard RNA was as follows.

(sequence) 5' GAA UAC AA-(bases 11 to 300 in HCV RNA) 3' (nucleotides 1–8 of SEQ ID NO:7)

As the standard DNA, a double stranded-DNA consisting of a DNA strand having the following sequence and a complementary strand was used.

(sequence) 5' ATT TAG GTG ACA CTA TAG AAT ACA A-(bases 11 to 300 in HCV cDNA)-3' (nucleotides 1–25 of SEQ ID NO:6)

After the procedure, each reaction solution was incubated at 65° C. for 30 minutes. 6 µl of the three kinds of reaction solutions, the standard RNA (69 ng/µl) and the standard DNA (6 ng/µl) were pored into three tubes each. To one of them, 0.6 µl of RNaseA (0.5 mg/ml) was added, to another one, 0.6 µl of DNaseI (1 mg/ml) was added, and to the remaining one, nothing was added. The three tubes of each set were incubated at 37° C. for 1 hour, and 5 µl of each reaction solution was subjected to 2% agarose gel electrophoresis. After the electrophoresis, the agarose gel was stained with 10,000-fold diluted SYBR Green II (Takara Shuzo Co., Ltd.) for 30 minutes. The compositions of the reaction solutions with the standard RNA (69 ng/µl) and the standard DNA (6 ng/µl) were the same as the composition of the other reaction solutions obtained by the procedure in Example 7 except that the enzymes were omitted.

Figure 8:
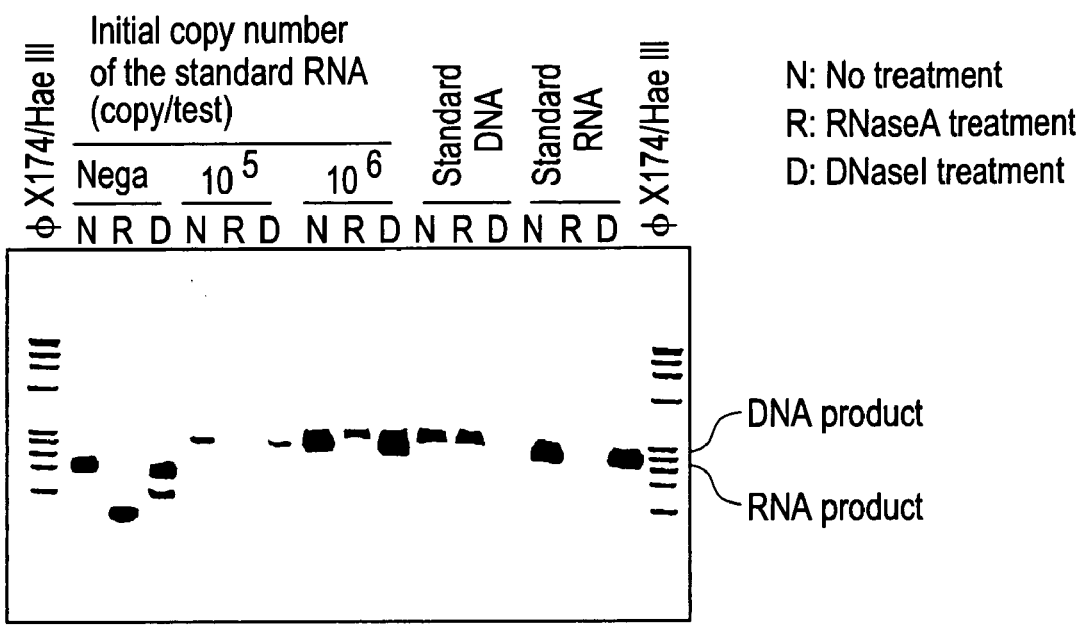
FIG. 8 shows the results of the 2% agarose electrophoresis of the products of the reactions using various concentrations of the standard RNA ($10^6$ copies/5 μl) after RNaseA or DNaseI treatment in Example 8. The DNA product and the RNA product are pointed.

FIG. 8 shows that the RNA product obtained by DNase I treatment of the DNA product from $10^6$ copies of the target standard RNA corresponded to 345 ng of the standard RNA in terms of band density. The band of the RNA product obtained by the DNase I treatment agreed with band of the standard RNA in terms of mobility.

On the other hand, the band obtained by amplification of $10^6$ copies of the target standard RNA followed by RNaseA treatment of the RNA product almost agreed with the standard DNA in terms of mobility.

Thus, both the RNA product and the DNA product were synthesized from the target RNA simultaneously.

EXAMPLE 9

Time Courses of RNA Production and DNA Production

The time courses of DNA production and RNA production were followed. A reaction solution having the following composition was prepared, and 33 µl of the reaction solution was pored into 10 PCR tubes 61 mM tris-acetate (pH 8.1)
20.5 mM magnesium acetate 189.2 mM potassium acetate
21.7% DMSO
12% sorbitol
15 mM dithiothreitol
1.5 mM each of ATP, GTP, CTP and UTP
1.5 mM each of dATP, dGTP, dCTP and dTTP
151 µg/ml BSA
0.3 µM third single-stranded oligo DNA
(sequence) 5' ATT TAG GTG ACA CTA TAG AAT ACA ACA CTC CAC CAT AGA TCA CTC CCC TG 3' (SEQ ID NO:1)
0.3 µM second single-stranded oligo DNA
(sequence) 5' ACT CGC AAG CAC CCT ATC A 3' (SEQ ID NO:2)

Then, 8.3 µl of a standard RNA ($10_6$ copies/5 µl) or TE buffer as the negative control was pored into five tubes. The standard RNA had the following sequence.
(sequence) 5' GAA UAC AA-(bases from 11 to 300 in HCV RNA) 3' (nucleotides 1–8 of SEQ ID NO:7)

The reaction solutions were overlaid with 100 µl mineral oil and incubated at 65° C. for 10 minutes, and then the tubes were allowed to stand still in ice-cold water for 5 minutes. After 10 minutes of incubation at 44° C., 8.6 µl of a mixed solution of the following enzymes was added. After 0, 1, 2, 3 and 4 hours of reaction at 44° C., one tube for each of the standard RNA and the negative control was withdrawn and transferred into ice.

32.8 U/µl commercially available SP6 RNA polymerase (Takara Shuzo Co., Ltd.)
11.8 U/µl commercially available RNase inhibitor (Takara Shuzo Co., Ltd.)
8.2 U/µl AMV reverse transcriptase (Takara Shuzo Co., Ltd.), as an RNA-dependent DNA polymerase and as a DNA-dependent DNA polymerase 5 µl of the reaction solution in each tube was subjected to 2% agarose electrophoresis. After the electrophoresis, the agarose gel was stained with 10,000-fold diluted SYBR Green II (Takara Shuzo Co., Ltd.) for 30 minutes and photographed. Then, the band densities (OD) in the photograph were measured with a densitometer.

The rest of each reaction solution was heated at 65° C. for 20 minutes, and 10 µl of each reaction solution were pored into three tubes. To one of them, 1 µl of RNaseA (0.5 mg/ml) was added, to another one, 1 µl of DNaseI (1 mg/ml) was added, and to the remaining one, 1 µl of TE buffer was added. All the three tubes of each set were incubated at 37° C. for 1 hour, and then 5 µl of each reaction solution was subjected to 2% agarose gel electrophoresis. After the electrophoresis, the gel was stained with 10,000-fold diluted SYBR Green II (Takara Shuzo Co., Ltd.) for 30 minutes and photographed. Then the band densities (OD) in the photograph were measured with a densitometer.

Figure 9:
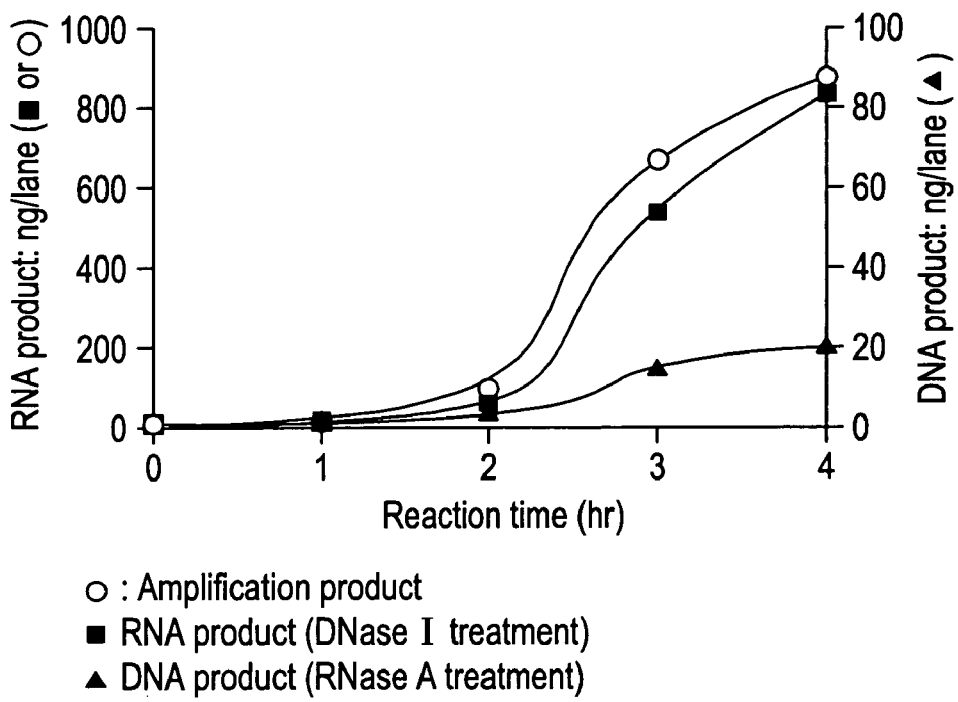
FIG. 9 shows the results of densitometric quantification of the products from the standard RNA ($10^6$ copies/5 μl) at various reaction times after RNaseA or DNaseI treatment followed by 2% agarose gel electrophoresis in Example 9.

FIG. 9 shows the time chart of DNA production and RNA production determined from the band densities in the electrophoretogram. The RNA production was about 40 times greater than the DNA production. Further, both the RNA production and the DNA production suddenly increased 2 hours after the initiation of the reaction. Thus, both RNA production and DNA production by the method of the present invention showed similar amplification curves.

EXAMPLE 10

Assay of Amplification Product Using Fourth Single-stranded Oligo DNA

An RNA product in reaction solutions was assayed by measuring the fluorescent signals by using a fourth single-stranded oligo RNA. Firstly, 20 µl of a reaction solution having the following composition was pored into 30 PCR tubes.
60 mM tris-acetate (pH 8.1)
20.3 mM magnesium acetate
187.5 mM potassium acetate
22.5% DMSO
12% sorbitol
1.5 mM each of ATP, GTP, CTP and UTP
1.5 mM each of dATP, dGTP, dCTP and dTTP
150 µg/ml BSA
0.3 µm third single-stranded oligo DNA
(sequence) 5' ATT TAG GTG ACA CTA TAG AAT ACA ACA CTC CAC CAT AGA TCA CTC CCC TG3' (SEQ ID NO:1)
0.3 µM second single-stranded oligo DNA
(sequence) 5' ACT CGC AAG CAC CCT AT-C A 3' (SEQ ID NO:2)

Then, 5 µl of a standard RNA ($10_6$ copies/5 µl) and TE buffer as a negative control were added to 15 tubes, respectively. The standard RNA had the following sequence.
(sequence) 5' GAA UAC AA-(bases 11 to 300 in HCV RNA) 3' (nucleotides 1–8 of SEQ ID NO:7)

The reaction solutions were overlaid with 100 µl mineral oil and incubated at 65° C. for 10 minutes, and then the tubes were allowed to stand still in ice-cold water for 5 minutes. After 10 minutes of incubation at 44° C., 5 µl of a mixed solution of the following enzymes was added. After 0, 1, 2, 3 and 4 hours of reaction at 44° C., three tube for each of the standard RNA and the negative control were withdrawn and transferred into ice.

36 U/µl commercially available SP6 RNA polymerase (Takara Shuzo Co., Ltd.)
12 U/µl commercially available RNase inhibitor (Takara Shuzo Co., Ltd.)
9 U/µl AMV reverse transcriptase (Takara Shuzo Co., Ltd.), as an RNA-dependent DNA polymerase and as a DNA-dependent DNA polymerase 5 µl of the reaction solution in each tube was subjected to 2% agarose electrophoresis. After the electrophoresis, the reaction solutions in the three tubes withdrawn at each reaction time were mixed, and 5 µl of each mixture was subjected to 2% agarose gel electrophoresis. After the electrophoresis, the agarose gel was stained with 10,000-fold diluted SYBR Green II (Takara Shuzo Co., Ltd.) for 30 minutes and photographed.

To 50 µl of each mixture, 100 µl of measuring buffer having the following composition was added.
40 mM tris-acetate (pH 8.1)
13 mM magnesium acetate
125 mM potassium acetate
10 mM dithiothreitol
2 U/µl RNase inhibitor
37.5 nM fourth single-stranded oligo DNA (hereinafter referred to as YO-271)
(sequence) 5'CTC GC*G GGG GCT G 3' (SEQ ID NO:5)
(* indicates the site labeled with the fluorescent intercalative dye, oxazole yellow. The sequence of bases 1 to 11 in the DNA moiety is complementary to the sequence of bases 223 to 233 in HCV cDNA. The fluorescent dye was linked to the DNA moiety as described in Nucleic Acids Research, 24(24), 4992–4997(1996) for YO-YPF-271. For the structure of YO-271, FIG. 19 should be referred to).

The reaction solutions were incubated at 65° C. for 15 minutes and suddenly cooled in ice-cold water for 5 minutes.

Then the reaction solutions were incubated at 37° C. for 10 minutes and poured into fluorometric cuvettes preheated to 37° C., and the fluorescent intensities were measured at an excitation wavelength of 490 nm and an emission wavelength of 510 nm.

FIG. 10 shows the results of the electrophoresis, and FIG. 11 shows the results of the measurements of the fluorescent signals from the fourth single-stranded oligo DNA (YO-271). As is evident from FIG. 11, the fluorescent signal from YO-271 increased suddenly in 2 hours for the standard RNA, whereas there was no increase in the fluorescence intensity with a negative control. Thus, use of the fourth single-stranded oligo DNA enabled to specific assay of the amplification product.

EXAMPLE 11

Modification of the 3' End of Fourth Single-stranded Oligo DNA

During synthesis of a single-stranded RNA in the presence of a fourth single-stranded oligo DNA, elongation of the DNA from the 3' end by the action of a coexisting RNA-dependent RNA polymerase can results in increase in a non-specific fluorescent signal. Therefore, the 3' end of the oligo DNA was modified by treatment with terminal transferase (TdT) (addition of ddTTP), and its effect was examined.

TdT treatment was conducted in a reaction solution (total volume 50 μl) having the following composition at 37° C. for 1 hour.

100 mM sodium cacodylate buffer (pH 7.2)
1 mM cobalt chloride
0.1 mM dithiothreitol
0.5 mM ddTTP
0.6 U/μl TdT (Takara Shuzo Co., Ltd.)
37.3 μM fourth single-stranded oligo DNA (YO-271)

The modification product was recovered by phenol-chloroform extraction followed by purification from the aqueous layer using a commercial column (chroma spin-10, tradename, Toyobo Co., Ltd.) and determined by OD260 measurement.

The resulting TdT-treated YO-271 and non-treated YO-271 were used for measurement of fluorescent signals in the present invention.

50 μl of reaction solutions having the following composition (containing non-treated YO-271 or TdT-treated YO-271) were pored into 10 tubes, respectively.

69 mM tris-acetate (pH 8.1)
20.3 mM magnesium acetate
187.5 mM potassium acetate
21.5% DMSO
12% sorbitol
15 mM dithiothreitol
1.5 mM each of ATP, GTP, CTP and UTP
1.5 mM each of dATP, dGTP, dCTP and dTTP
150 μg/ml BSA
0.3 μM third single-stranded oligo DNA
(sequence) 5' ATT TAG GTG ACA CTA TAG AAT ACA ACA CTC CAC CAT AGA TCA CTC CCC TG 3' (SEQ ID NO:1)
0.3 μM second single-stranded oligo DNA
(sequence) 5' ACT CGC AAG CAC CCT ATC A 3' (SEQ ID NO:2)
112.5 nM TdT-treated YO-271 or non-treated YO-271

Then, 12.5 μl of a standard RNA ($10^6$ copies/5 μl) or TE buffer as a negative control was added to five tubes, respectively. The standard RNA had the following sequence.

(sequence) 5' GAA UAC AA-(bases 11 to 300 in HCV RNA) 3' (nucleotides 1–8 of SEQ ID NO:7)

The reaction solutions were overlaid with 100 μl mineral oil and incubated at 65° C. for 10 minutes, and then the tubes were allowed to stand still in ice-cold water for 5 minutes. After 10 minutes of incubation at 44° C., 12.5 μl of a mixed solution of the following enzymes was added. After reaction at 40° C. for 0, 1, 2, 3 and 4 hours, tubes were withdrawn and transferred into ice-cold water for the standard RNA and negative control.

34.2 U/μl commercially available SP6 RNA polymerase (Takara Shuzo Co., Ltd.)
12 U/μl commercially available RNase inhibitor (Takara Shuzo Co., Ltd.)
8.4 U/μl AMV reverse transcriptase (Takara Shuzo Co., Ltd.) as an RNA-dependent DNA polymerase and as a DNA-dependent DNA polymerase A 50 μl aliquot of each reaction solution was mixed with 100 μl of dilution buffer having the following composition, incubated at 44° C. for 5 minutes and transferred into a fluorometric cuvette preheated at 44° C., and the fluorescence intensity was measured at an excitation wavelength of 490 nm and an emission wavelength of 510 nm.

40 mM tris-acetate (pH 8.1)
13 mM magnesium acetate
125 mM potassium acetate
10 mM dithiothreitol
2 U/μl RNase inhibitor FIG. 12 and FIG. 13 show the results with the non-treated and TdT-treated YO-271, respectively.

In the case of the non-treated YO-271, there was an increase in the fluorescent signal in the presence of the negative control, and the fluorescent signal in the presence of the negative control was not significantly different from that in the presence of the standard RNA. On the other hand, in the case of the ddTTP-treated YO-271, there was a significant difference between the fluorescent signal in the presence of the negative control and in the presence of the standard RNA. Thus, for RNA synthesis in the presence of the fourth single-stranded oligo DNA in the present invention, it is preferred to modify the 3' end of the DNA so as to prevent elongation of the DNA from the 3' end by the action of the RNA-dependent DNA polymerase

EXAMPLE 12

RNA or DNA Synthesis in the Presence of Fourth Single-stranded Oligo DNA

The effects of the ddTTP-treated YO-271 prepared in Example 11 on RNA or DNA synthesis in the presence of a fourth single-stranded oligo DNA were examined. 50 μl of a reaction solution having the following composition was pored into 10 tubes.

60 mM tri-acetate (pH 8.1)
2.3 mM magnesium acetate
187.5 mM potassium acetate
21.5% DMSO
12% sorbitol
15 mM dithiothreitol
1.5 mM each of ATP, GTP, CTP and UTP
1.5 mM each of dATP, dGTP, dCTP and dTTP
150 μg/ml BSA
0.3 μM third single-stranded oligo DNA (sequence) 5' ATT TAG GTG ACA CTA TAG AAT ACA ACA CTC CAC CAT AGA TCA CTC CCC TG 3' (SEQ ID NO:1)

0.3 µM second single-stranded oligo DNA (sequence) 5' ACT CGC AAG CAC CCT ATC A 3' (SEQ ID NO:2)

112.5 nM TdT-treated YO-271

Then, 12.5 µl of a standard RNA (10⁶ copies/5 µl) or TE buffer as a negative control was added to five tubes, respectively. The standard RNA had the following sequence.

(sequence) 5' GAA UAC AA-(bases from 11 to 300 in HCV RNA) 3' (nucleotides 1–8 of SEQ ID NO:7)

The reaction solutions were overlaid with 100 µl mineral oil and incubated at 65° C. for 10 minutes, and then the tubes were allowed to stand still in ice-cold water for 5 minutes. After 10 minutes of incubation at 44° C., 12.5 µl of a mixed solution of the following enzymes was added. After reaction at 40° C. for 0, 1, 2, 3 and 4 hours, tubes were withdrawn and transferred into ice-cold water for the standard RNA and negative control.

34.2 U/µl commercially available SP6 RNA polymerase (Takara Shuzo Co., Ltd.)

12 U/µl commercially available RNase inhibitor (Takara Shuzo Co., Ltd.)

8.4 U/µl AMV reverse transcriptase (Takara Shuzo Co., Ltd.) as an RNA-dependent DNA polymerase and as a DNA-dependent DNA polymerase 5 µl of the reaction solution in each tube was subjected to 2% agarose gel electrophoresis. After the electrophoresis, the agarose gel was stained with 10,000-fold diluted SYBR Green II (Takara Shuzo Co., Ltd.) for 30 minutes and photographed. The band densities (OD) in the photograph was measured with a densitometer.

FIG. 14 shows the results of the electrophoresis, and FIG. 15 shows the results of the OD measurement of the electrophoretogram. In the presence of the standard RNA, the amplification product increased with time, whereas in the presence of the negative control, there was no increase of the amplification product. Thus, the presence of the fourth single-stranded oligo DNA did not inhibit RNA synthesis in the present invention.

EXAMPLE 13

Analysis of the Time Course of the Amount of Amplification Product by Using Fourth Single-stranded Oligo DNA RNA production was monitored by using the ddTTP-treated YO-271 prepared in Example 11 as the fourth single-stranded oligo DNA over a period of time. Firstly, 50 µl of a reaction solution having the following composition was pored into 10 tubes.

60 nM tris-acetate (pH 8.1)

20.3 mM magnesium acetate 187.5 mM potassium acetate 21.5% DMSO

12% sorbitol 15 mM dithiothreitol 1.5 mM each of ATP, GTP, CTP and UTP 1.5 mM each of dATP, dGTP, dCTP and dTTP 150 µg/ml BSA 0.3 µM third single-stranded oligo DNA (sequence) 5' ATT TAG GTG ACA CTA TAG AAT ACA ACA CTC CAC CAT AGA TCA CTC CCC TG 3' (SEQ ID NO:1)

0.3 µM second single-stranded oligo DNA (sequence) 5' ACT CGC AAG CAC CCT ATC A 3' (SEQ ID NO:2)

112.5 nM TdT-treated YO-271

Then, 12.5 µl of a standard RNA (10⁶ copies/5 µl) or TE buffer as a negative control was added to five tubes, respectively. The standard RNA had the following sequence.

(sequence) 5' GAA UAC AA-(bases 11 to 300 in HCV RNA) 3' (nucleotides 1–8 of SEQ ID NO:7)

The reaction solutions were overlaid with 100 µl of mineral oil and incubated at 65° C. for 10 minutes, and then the tubes were allowed to stand still in ice-cold water for 5 minutes. After 10 minutes of incubation at 44° C., 12.5 µl of a mixed solution of the following enzymes was added. After reaction at 40° C. for 0, 1, 2, 3 and 4 hours, tubes were withdrawn and transferred into ice-cold water for the standard RNA and negative control.

34.2 U/µl commercially available SP6 RNA polymerase (Takara Shuzo Co., Ltd.)

12 U/µl commercially available RNase inhibitor (Takara Shuzo Co., Ltd.)

8.4 U/µl AMV reverse transcriptase (Takara Shuzo Co., Ltd.) as an RNA-dependent DNA polymerase and as a DNA-dependent DNA polymerase A 50 µl aliquot of each reaction solution was mixed with 100 µl of dilution buffer having the following composition, incubated at 44° C. for 5 minutes and transferred into a fluorometric cuvette preheated at 44° C., and the fluorescence intensity was measured at an excitation wavelength of 490 nm and an emission wavelength of 510 nm.

40 mM tris-acetate (pH 8.1)

13 mM magnesium acetate 125 mM potassium acetate 10 mM dithiothreitol

2 U/µl RNase inhibitor

FIG. 16 shows the results of the fluorescence measurement. In the presence of the standard RNA, the fluorescence intensity increased with the elapse of time, whereas in the presence of the negative control, the fluorescence intensity did not increase. The fluorescence profile almost agreed with the results of the electrophoretic quantification in Example 12. Thus, use of the fourth single-stranded oligo DNA made it possible to follow the time course of specific amplification (RNA synthesis)

EXAMPLE 14

Monitoring of a Fluorescent Signal Using Fourth Single-stranded Oligo DNA

The fluorescence intensity of the ddTTP-treated Yo-271 prepared in Example 11 in the presence of known concentrations of a target RNA was monitored. Firstly, 50 µl of a reaction solution having the following composition were pored into 17 PCR tubes.

60 mM tris-acetate (pH 8.1)

20.3 mM magnesium acetate 187.5 mM potassium acetate 21.5% DMSO

12% sorbitol 15 mM dithiothreitol 1.5 mM each of ATP, GTP, CTP and UTP 1.5 mM each of dATP, dGTP, dCTP and dTTP 150 µg/ml BSA 0.3 µM third single-stranded oligo DNA (sequence) 5' ATT TAG GTG ACA CTA TAG AAT ACA ACA CTC CAC CAT AGA TCA CTC CCC TG 3' (SEQ ID NO:1)

0.3 μM second single-stranded oligo DNA (sequence) 5' ACT CGC AAG CAC CCT ATC A 3' (SEQ ID NO:2)

112.5 nM TdT-treated YO-271

Then, 12.5 μl of a standard RNA ($10^4$ copies or $10^5$ copies/5 μl) and TE buffer as a negative control were pored into four tubes each. Separately, 12.5 μl of the standard RNA ($10^6$ copies/5 μl) was pored into five tubes.

The standard RNA had the following sequence.

(sequence) 5' GAA UAC AA-(bases 11 to 300 in HCV RNA) 3' (nucleotides 1–8 of SEQ ID NO:7)

The reaction solutions were overlaid with 100 μl mineral oil and incubated at 65° C. for 10 minutes, and then the tubes were allowed to stand dtill in ice-cold water for 5 minutes. After 10 minutes of incubation at 44° C., 12.5 μl of a mixed solution of the following enzymes was added. After reaction at 44° C. for 0, 1 (only for $10^6$ copies/5 μl of the standard RNA), 2, 3 and 4 hours, one tube was withdrawn and transferred into ice-cold water for the standard RNA and the negative control, respectively.

34.2 U/μl commercially available SP6 RNA polymerase (Takara Shuzo Co., Ltd.)

12 U/μl commercial available RNase inhibitor (Takara Shuzo Co., Ltd.)

8.4 U/μl AMV reverse transcriptase (Takara Shuzo Co., Ltd.) as an RNA-dependent DNA polymerase and as a DNA-dependent DNA polymerase A 50 μl aliquot of each reaction solution was mixed with 100 μl of dilution buffer having the following composition, incubated at 44° C. for 5 minutes and transferred into a fluorometric cuvette preheated at 44° C., and the fluorescence intensity was measured at an excitation wavelength of 490 nm and an emission wavelength of 510 nm.

40 mM tris-acetate (pH 8.1)
13 mM magnesium acetate
125 mM potassium acetate
10 mM dithiothreitol
1 U/μl RNase inhibitor FIG. 17 shows fluorescence intensities measured at the respective reaction times after subtraction of the background fluorescence intensity. The plot of the fluorescence intensities at the reaction time of 3 hours against the initial concentrations of the target RNA based on the fluorescence profiles (FIG. 18) shows concentration-dependent fluorescence enhancement. Thus, a calibration curve which shows the correlation between the initial concentration of the target RNA and fluorescence enhancement was obtained on the base of the amplification curve obtained by monitoring the fluorescence intensity. Thus, by measuring fluorescence intensity for a sample containing the target RNA at an unknown concentration, the initial amount of the target RNA could be determined.

As described so far, the present invention enables assay of a single-stranded RNA containing a specific nucleic acids sequence in a sample at almost constant temperature without repetitious rapid heating and cooling of reaction solutions. Further, the method of the present invention enables high sensitive specific homogeneous assay of a target nucleic acid without using a support.

In the present invention, from a trace amount of a single-stranded RNA in a sample, a double-stranded DNA having a promoter region for a DNA-dependent RNA polymerase at one end is synthesized, and the double-stranded DNA gives rise to multiple RNA single strands. The synthesized single-stranded RNA participates in the next round of synthesis of the double-stranded DNA. Consequently, the single-stranded RNA synthesized in the series of reactions as an intermediate drastically increases with the elapse of time. However, because the rate of the RNA synthesis and the final amount of the synthesized RNA depend on the amount of the target RNA in the sample, assay of the target RNA is possible by measurement of the amount of the synthesized RNA.

The fourth single-stranded oligo DNA in the present invention enhances the fluorescence intensity on hybridization with the single-stranded RNA in the reaction solution, and thereby enables determination of the initial amount of the target RNA in the sample by measuring the fluorescent intensity of the reaction solution.

Thus, the assay method of the present invention can be conducted at constant temperature because the reactions proceed through binding of primers to the single-stranded RNA and DNA synthesized as intermediates, and can be automated easily because it does not require repetitious rapid heating and cooling of reaction solutions for priming unlike PCR. Further, in the present invention, the use of the fourth single-stranded oligo DNA makes is possible to monitor RNA synthesis by measuring the fluorescent intensity during the single-stranded RNA. Therefore, it is possible to provide a simple one-step method for accurate speedy homogeneous qualitative and quantitative assay of a target RNA useful for clinical diagnosis without need of electrophoresis or sandwich assay of the reaction product.

On the basis of the multiplication of a specific RNA sequence at constant temperature, the present invention also provides a simple method for producing RNA which can be conducted under milder conditions than conventional chemical synthesis and RT-PCR. Thus, a maximal reaction efficiency was obtained in the presence of potassium acetate at a final concentration of from 110 to 130 mM.

EXAMPLE 4

Effects of Sorbitol

The optimum sorbitol concentration for the present invention was studied. 20 μl of reaction solutions having the following composition were pored into PCR tubes.

60 mM tris-acetate (pH 8.1)
20.3 mM magnesium acetate
187.5 mM potassium acetate
15% DMSO
22.5, 16.8, 13.5 or 11.3% sorbitol
(final concentration: 15, 11.3, 9 or 7.5%)
1.5 mMl each of ATP, GTP, CTP and UTP
1.5 mM each of dATP, dGTP, dCTP and dTTP
150 μg/ml BSA
0.3 μM second single-stranded oligo DNA (sequence) 5' ACT CGC AAG CAC CCT ATC A 3' (SEQ ID NO:2)

0.3 μM third single-stranded oligo DNA (sequence) 5' ATT TAG GTG ACA CTA TAG AAT ACA ACA CTC CAC CAT AGA TCA CTC CCC TG 3' (SEQ ID NO:1)

Then, 5 μl of a standard RNA ($10^3$ copies, $10^4$ copies, $10^5$ copies or $10^6$ copies/5 μl) or 5 μl of RNA-free TE buffer as a negative control was added. The standard RNA had the following sequence.

(sequence) 5' GAA UCA AA-(bases 11 to 300 in HCV RNA) 3' (nucleotides 1–8 of SEQ ID NO:7)

The reaction solutions were overlaid with 100 μl mineral oil and incubated at 65° C. for 10 minutes, and then the tubes were allowed to stand still in ice-cold water for 5 minutes. Then, 5 μl of a mixed solution of the following enzymes was added, and reaction was conducted at 45° C. for 4 hours.

36 U/μl commercially available SP6 RNA polymerase (Takara Shuzo Co., Ltd.)

12 U/μl commercially available RNase inhibitor (Takara Shuzo Co., Ltd.)

9 U/μl AMV reverse transcriptase (Takara Shuzo Co., Ltd.), as an RNA-dependent DNA polymerase and as a DNA-dependent DNA polymerase 5 μl of the reaction solutions were subjected to agarose gel electrophoresis. After the electrophoresis, the gel was stained with 10,000-fold diluted SYBR Green II (Takara Shuzo Co., Ltd.) for 30 minutes.

FIG. 3 shows the pattern on the stained gel. The clear bands of 300 bp were obtained in the presence of sorbitol at a final concentration of 7.5 to 11.3% even when the initial amount of the target nucleic acid was $10^3$ copies. Thus, the maximal reaction efficiency was obtained when the final sorbitol concentration was from 7.5 to 11.3%.

EXAMPLE 5

Amplification of Double-stranded DNA as Target Nucleic Acid

---

What is claimed is:

1. A method for assaying for a specific nucleic acid sequence that is within a target RNA, wherein said target RNA is a single-stranded RNA, said method comprising the following steps:

I. providing said target RNA comprising said specific nucleic acid sequence;
  II. hybridizing said target RNA to a reagent (A), which is a single-stranded oligo nucleic acid complementary to a sequence 5' of, and adjacent to, the 5' end of said specific nucleic acid sequence that is within the target RNA, which allows the target RNA to be cut at the 5' end of the specific nucleic acid sequence by the action of a reagent (D), which is a ribonuclease that degrades RNA in a DNA-RNA double-strand;
  III. cutting the target RNA at the 5' end of the specific nucleic acid sequence with reagent D to give a product;
  IV. hybridizing to said product of step (III), a reagent (B), which is a first single-stranded oligo DNA primer complementary to a sequence at the 3' end of said specific nucleic acid sequence;
  V. extending said first single-stranded oligo DNA primer to the 5' end of the specific nucleic acid sequence with a reagent (C), which is an RNA-dependent DNA polymerase and with a reagent (E), which is deoxynucleoside triphosphates, to form a DNA-RNA double-strand;
  VI. digesting the RNA strand of said DNA-RNA double-strand from step (V) with the reagent (D), to give a single-stranded DNA complementary to said specific nucleic acid sequence;
  VII. hybridizing to said single-stranded DNA from step (VI) a reagent (F) which is a second single-stranded oligo DNA primer having the following sequences, in the following order, beginning at the 5' end and proceeding in a 5' to 3' direction: i) a promoter sequence for a DNA-dependent RNA polymerase, ii) an enhancer sequence for said promoter sequence, and iii) a sequence at the 5' end of said specific nucleic acid sequence;
  VIII. extending said second oligo DNA primer to the 5' end of said single-stranded DNA with a reagent (G), which is a DNA-dependent DNA polymerase and with said reagent (E);
  IX. synthesizing a single-stranded RNA from said promoter sequence with a reagent (H), which is a DNA-dependent RNA polymerase and a reagent (I), which is ribonucleoside triphosphates;
  X. either:
    (a) cycling said single-stranded RNA from step (IX) to step (IV), or
    (b) hybridizing to said single-stranded RNA from step (IX) a reagent (J), which is a single-stranded oligo DNA complementary to said specific nucleic acid sequence, labeled so that it gives off a measurable fluorescent signal upon hybridization with a nucleic acid containing said specific nucleic acid sequence; and
  XI. after addition of reagents (A) to (J), measuring at least once a fluorescent signal from said hybrid formed in step (X) (b);
  wherein said reagents (A) to (J) are added to a reaction vessel one by one, in functional combinations, or all at once,
  thereby assaying for a specific nucleic acid sequence that is within a target RNA by measurement of a fluorescent signal.

2. The method according to claim 1, wherein the reagent (A) is a DNA, and the method further comprises adding an RNaseH and deactivating the RNaseH by heating or by addition of an inhibitor prior to addition of the reagent (B).

3. The method according to claim 2, wherein addition of the reagent (A) is followed by simultaneous addition of the reagents (B) to (I), and then by addition of the reagent (J).

4. The method according to claim 2, wherein addition of the reagent (A) is followed by simultaneous addition of the reagents (B) to (J).

5. The method according to claim 1, wherein the reagent (C), an RNA-dependent DNA polymerase, is also the reagent (D), a ribonuclease that degrades RNA in a DNA-RNA double strand.

6. The method according to claim 1, wherein an enzyme having both an RNA-dependent DNA polymerase activity and a DNA-dependent DNA polymerase activity is used as both the reagents (C) and (G).

7. The method according to claim 6, wherein the enzyme is avian myoblastoma virus polymerase.

8. The method according to claim 1, wherein the first and second oligo DNA primers as the reagents (B) and (F) are used at concentrations of from 0.02 to 1 µM.

9. The method according to claim 1, wherein the DNA-dependent RNA polymerase as the reagent (H) is at least one enzyme selected from the group consisting of phage SP6 polymerase, phage T3 polymerase, and phage T7 polymerase.

10. The method according to claim 1, wherein the single-stranded oligo DNA as the reagent (J) is a DNA which is linked to a fluorescent intercalative dye so that the fluorescent intercalative dye changes its fluorescence characteristic upon hybridization of the DNA with another nucleic acid by intercalating into the resulting double strand.

11. The method according to claim 1, wherein the single-stranded oligo DNA as the reagent (J) is a DNA which has a 3' end sequence that is not complementary to the specific nucleic acid sequence or has a modified 3' end, and hybridizes to the nucleic acid of claim 1 having said specific nucleic acid sequence.

12. The method according to claim 10, wherein the single-stranded oligo DNA as the reagent (J) is a DNA which has a 3' end sequence that is not complementary to the specific nucleic acid sequence or has a modified 3' end, and hybridizes to the nucleic acid of claim 1 having said specific nucleic acid sequence.

13. The method according to claim 1, which further comprises a step of detecting or quantifying the target RNA in the sample based on the measured fluorescent signal or change in the measured fluorescent signal.

14. The method according to claim 1, wherein all the reagents are chloride-free.

15. The method according to claim 1, wherein prior to said step (X)(b) acetate is added as a reagent.

16. The method according to claim 15, wherein the acetate is magnesium acetate at a concentration of from 5 to 20 mM or potassium acetate at a concentration of from 50 to 200 mM.

17. The method according to claim 1, wherein prior to said step (X)(b) sorbitol is added as a reagent.

18. The method according to claim 1, wherein the temperature is selected from the range of from 35 to 60° C.

* * * * *